US011096903B2

(12) United States Patent
Park

(10) Patent No.: US 11,096,903 B2
(45) Date of Patent: Aug. 24, 2021

(54) USE OF PINOCARVEOL

(71) Applicant: INDUSTRY-ACADEMIC COOPERATION FOUNDATION, YONSEI UNIVERSITY, Seoul (KR)

(72) Inventor: Tae Sun Park, Seoul (KR)

(73) Assignee: INDUSTRY-ACADEMIC COOPERATION FOUNDATION, YONSEI UNIVERSITY, Seoul (KR)

(*) Notice: Subject to any disclaimer, the term of this patent is extended or adjusted under 35 U.S.C. 154(b) by 1 day.

(21) Appl. No.: 15/579,521

(22) PCT Filed: May 30, 2016

(86) PCT No.: PCT/KR2016/005721
§ 371 (c)(1),
(2) Date: Dec. 4, 2017

(87) PCT Pub. No.: WO2016/195357
PCT Pub. Date: Dec. 8, 2016

(65) Prior Publication Data
US 2018/0369162 A1 Dec. 27, 2018

(30) Foreign Application Priority Data
Jun. 3, 2015 (KR) .................. 10-2015-0078715

(51) Int. Cl.
A61K 31/045 (2006.01)
A61P 3/10 (2006.01)
A61P 3/04 (2006.01)
A61P 3/06 (2006.01)
A61P 1/16 (2006.01)
A23L 33/10 (2016.01)
A23L 33/105 (2016.01)
A23L 33/00 (2016.01)

(52) U.S. Cl.
CPC ............ *A61K 31/045* (2013.01); *A23L 33/10* (2016.08); *A23L 33/105* (2016.08); *A23L 33/40* (2016.08);
(Continued)

(58) Field of Classification Search
CPC ...... A61K 31/045; A23L 33/105; A23L 33/40; A23L 33/10; A61P 1/16; A61P 3/04;
(Continued)

(56) References Cited

U.S. PATENT DOCUMENTS

2004/0092583 A1 5/2004 Shanahan-Prendergast
2008/0233219 A1 9/2008 Karita
2011/0045069 A1* 2/2011 Ley .................. A61K 31/216
424/474

FOREIGN PATENT DOCUMENTS

KR 10-1078376 10/2011
KR 10-1186500 9/2012

OTHER PUBLICATIONS

Johns, Mitochondrial DNA and Disease, The New England Journal of Medicine, 1995, 333(10), pp. 638-644 (Year: 1995).*
(Continued)

*Primary Examiner* — Savitha M Rao
*Assistant Examiner* — Andrew P Lee
(74) *Attorney, Agent, or Firm* — Norton Rose Fulbright US LLP

(57) ABSTRACT

The present invention relates to a pharmaceutical composition comprising pinocarveol for preventing or treating metabolic diseases, and functional food composition using the pharmaceutical composition for improving or alleviating metabolic diseases. Pinocarveol according to the present invention reduces weight, visceral fat, and cholesterol concentration, improves blood liver function index, reduces blood sugar, and additionally inhibits a metabolic inflammation reaction, and thus can be effectively used ultimately as a medical or functional food composition exhibiting prevention or treatment activities for metabolic diseases selected from the group consisting of obesity, diabetes, dyslipidemia, and syndromes of fatty liver and insulin-resistance.

8 Claims, 18 Drawing Sheets
Specification includes a Sequence Listing.

(52) U.S. Cl.
CPC .................. *A61P 1/16* (2018.01); *A61P 3/04* (2018.01); *A61P 3/06* (2018.01); *A61P 3/10* (2018.01); *A23V 2002/00* (2013.01); *A23V 2200/328* (2013.01); *A23V 2200/332* (2013.01)

(58) Field of Classification Search
CPC .......... A61P 3/06; A61P 3/10; A23V 2002/00; A23V 2200/328; A23V 2200/332
See application file for complete search history.

(56) References Cited

OTHER PUBLICATIONS

Asnaashari, Essential Oil from Citrus aurantifolia Prevents Ketotifen-induced Weight-gain in Mice, Phytotherapy Research, 2010, 24 , pp. 1893-1897 (Year: 2010).*

Freeman et al., "Biology of disease: free radicals and tissue injury," *Lab Invest*, 47(5) 412-426, 1982.

International Search Report issued in International Application No. PCT/KR2016/005721, dated Sep. 8, 2016.

Kawamura et al., "Pathophysiological Concentrations of Glucose Promote Oxidative Modification of Low Density Lipoprotein by a Superoxide-dependent Pathway," *J Clin Invest*, 94:771-778, 1994.

Reaven, "Role of Insulin Resistance in Human Disease," *Diabetes*, 37: 1595-1607, 1988.

Shafi et al., "Antibacterial activity of *Syzygium cumini* and *Syzygium travancoricum* leaf essential oils," *Fitoterapia*, 73: 414-416, 2002.

Singh et al., "Phyto-pharmacotherapeutics of *Cyperus rotundus* Linn. (*Motha*): An Overview," *Indian Journal of Natural Products and Resources*, 3(4): 467-476, 2012.

* cited by examiner

Epididymal

Perirenal

Mesenteric

Retropertoneal

Chow     HFD     PD     Met     Sibu

USE OF PINOCARVEOL

CROSS-REFERENCE TO RELATED APPLICATIONS

This application is a national phase application under 35 U.S.C. § 371 of International Patent Application No. PCT/KR2016/005721, filed May 30, 2016, which claims priority to Korean Patent Application No. 10-2015-0078715, filed Jun. 3, 2015, the contents of which applications are incorporated by reference herein in their entirety.

STATEMENT OF GOVERNMENT SUPPORT

The present invention was conducted as Project No. 1130373 under the support of the Ministry of Agriculture, Food and Rural Affairs of Korea, and the research management agency of the above project is Korea Institute of Planning and Evaluation for Technology in Food, Agriculture and Forestry, the name of the research business is "Technology Commercialization Support Business", the name of the research project is "Development of Individual Types of Health Functional Food Raw Ingredients for Controlling Weight and Alleviating Metabolic Diseases Using Extracts from *Artemisia Iwayomogi*", the research institution is Industry-Academic Cooperation Foundation at Yonsei University, and the research period is from Dec. 4, 2013 to Dec. 3, 2016.

The present invention was also conducted as Project No. 2015R1A5A6001906 under the support of the Ministry of Education, Science and Technology of Korea, the research management agency of the above project is National Research Foundation of Korea, the name of the research business is "Leading Research Center Promotional Business Science Research Center (SRC)", the name of the research project is "Food and Nutritional Genomics Research Center", the research institution is Industry-Academic Cooperation Foundation at Kyungpook National University, and the research period is from Mar. 1, 2015 to Feb. 28, 2016.

FIELD OF THE DISCLOSURE

The present invention relates to a pharmaceutical composition for preventing or treating metabolic diseases including pinocarveol as an active ingredient, and a functional food composition for preventing or alleviating metabolic diseases.

DESCRIPTION OF RELATED ART

As intra-abdominal obesity of modern people increases due to changes in the living environment, the occurrence of metabolic syndromes accompanied with diabetes, high blood pressure, dysfunction of lipid metabolism, insulin resistance, or the like has rapidly increased. These diseases increase the risk of mutual occurrences and are common diseases which are associated with multifactorial metabolic changes such as aging, stress, lowered immune functions, and the like. Obesity causes, in addition to problems of appearance, chronic diseases such as fatty liver, high blood pressure, diabetes, cardiovascular diseases, and the like.

About 1.7 billion people corresponding to approximately 25% of the world population are currently overweight (BMI >25), and more than 300 million people of the Western society including 120 million people of the United States, Europe, and Japan which are the major markets are classified as obese patients (BMI >30). Among the OECD countries, the United States has the highest obesity rate with 31% of obese patients in the entire population, and the ratio of obese patients among the entire population is shown to be high in the following order of Mexico (24%), the United Kingdom (23%), Greece (22%), Australia (22%), New Zealand (21%), Hungary (19%), Canada (14%), Spain (13%), Ireland (13%), Germany (13%), Portugal (13%), Finland (13%), Turkey (12%), and Belgium (12%). 70 million people of China are obese, the market related to weight control is rapidly expanding, and the total market size is estimated to be around 10 billion yuan. Furthermore, currently, 1 out of 5 children in the world is believed to have child obesity, and this number is rapidly increasing, and as a result, child obesity is becoming a serious social problem. Due to high blood cholesterol and high neutral fat level, childhood obesity is the main cause of diabetes, high blood pressure, stroke, and the like, which are referred to as lifestyle diseases, and 80% or more of obese children grow up to have adult obesity, in which problems of health caused by obesity may seriously worsen as they age. In addition, as fat accumulates, the secretion of sex hormones is triggered to expedite precocious puberty and result in developmental disorders, which is a developmental suppressing factor by affecting blood circulation and nutritional supply.

Non-alcoholic fatty liver disease (hereinafter referred to as NAFLD) refers to a disease in which neutral fat is accumulated in the liver regardless of drinking alcohol and includes steatosis and non-alcoholic steatohepatitis (NASH). Although steatosis is clinically regarded as a benign disease with favorable prognosis, NASH is a progressive liver disease accompanied by inflammation or fibrosis along with fatty liver and is recognized as a precursor disease causing cirrhosis of the liver or liver cancer.

Obesity and insulin resistance are main risk factors of non-alcoholic fatty liver disease. As risk factors for the progression of liver fibrosis, there are, for example, obesity (BMI >30), liver function index ratio in blood (AST/ALT >1), and diabetes, and in particular, a hepatitis C carrier who also has a non-alcoholic fatty liver may progress to liver cancer, and therefore, the prevention and treatment therefor is necessary. 69 to 100% of non-alcoholic fatty liver patients are obese patients, and 20 to 40% of obese patients have a non-alcoholic fatty liver, and in particular, the prevalence of liver diseases of male obese patients is exhibited as higher than that of female obese patients. Not only obese patients but also 3 to 30% of adults with normal weights are reported to have non-alcoholic fatty liver lesion in the Western society. The prevalence of non-alcoholic fatty liver in Japan with similar diet to that of Korea is estimated to be about 20%, and 1% thereof is presumed to be NASH. Non-alcoholic fatty liver is problematic in adults as well as in obese children. 10 to 77% of obese children (in Europe, the United States, and Asia) have non-alcoholic fatty liver lesions, and this is because obesity is the most important risk factor of non-alcoholic liver diseases.

As anti-obesity drugs which are currently available in Korea and abroad, there are Xenical (Roche Korea) containing orlistat as a main ingredient which has been approved by FDA, Reductil (Ilsung Pharmaceuticals) containing sibutramine as an ingredient, Exollise (Guju Pharmaceuticals) containing a catechol component from green tea as an ingredient, and the like. In the case of Xenical suppressing lipase action, gastrointestinal side effects such as steatorrhea, gas production, reduction in absorption of fat-soluble vitamins, and the like occur, and in the case of Reductil, as the concentrations of serotonin and noradrenalin are increased in the sympathetic nervous system, side effects such as headache, thirst, loss of appetite, insomnia, constipation, and the like occur. Besides, among the products developed as anti-obesity medications so far, there are many products that have been prohibited from being sold in the market due to serious side effects. For example, aminophylline, despite its excellent digestive effect of body fat, has been reported to cause a wide range of side effects in the mental and nervous system, the circulatory system, and the digest system, and the sale of fenfluramine, dexfenfluramine, topiramate, ephedrine, and the like was prohibited because these drugs were determined as inappropriate drugs for treating obesity. As conventional synthetic medicines show limitations due to side effects, the demand for development of novel compositions for treating obesity suitable for treating chronic diseases, which is safe and can be administered in long term is increasing.

Throughout the entire specification, many research papers and patent documents are referenced and citations thereof are indicated. The disclosed contents of the cited research papers and patent documents are incorporated herein by reference in their entirety to more clearly describe the level of the technical field to which the present invention belongs and the contents of the present invention.

Prior patent documents of the present invention include Korean Registered Patent No. 1078376 and Korean Registered Patent No. 1186500.

SUMMARY OF THE INVENTION

The present inventors have made great efforts in research to develop compounds having preventive or treatment activity for metabolic diseases such as obesity, diabetes, dyslipidemia, fatty liver, insulin resistance syndrome, and the like. As a result, it was confirmed that since pinocarveol reduces body fat and blood sugar level and significantly improves various indicators of metabolic diseases, pinocarveol exhibits effects of preventing, ameliorating, and treating the metabolic diseases, and thereby the present invention was completed.

Therefore, an object of the present invention is to provide a pharmaceutical composition for preventing or treating a metabolic disease, including pinocarveol as an active ingredient, wherein the metabolic disease is selected from the group consisting of obesity, diabetes, dyslipidemia, fatty liver, and insulin resistance syndrome.

Another object of the present invention is to provide a functional food composition for preventing or ameliorating a metabolic disease, including pinocarveol as an active ingredient, wherein the metabolic disease is selected from the group consisting of obesity, diabetes, dyslipidemia, fatty liver, and insulin resistance syndrome.

Still another object of the present invention is to provide a method of preventing or treating a metabolic disease, wherein the metabolic disease is selected from the group consisting of obesity, diabetes, dyslipidemia, fatty liver, and insulin resistance syndrome.

Other objects and advantages of the present invention are more clearly described by the detailed description of the invention, the scope of the claims, and the figures, as shown below.

According to an embodiment of the present invention, provided is a pharmaceutical composition for preventing or treating a metabolic disease, including pinocarveol as an active ingredient, wherein the metabolic disease is selected from the group consisting of obesity, diabetes, dyslipidemia, fatty liver, and insulin resistance syndrome.

The present inventors have made great efforts in research to develop compounds having preventive or treatment activity for metabolic diseases such as obesity, diabetes, dyslipidemia, fatty liver, insulin resistance syndrome, and the like. As a result, it was confirmed that since pinocarveol reduces body fat and blood sugar level and significantly improves various indicators of metabolic diseases, pinocarveol exhibits effects of preventing, ameliorating, and treating the metabolic diseases.

As used herein, the term "pinocarveol" is a bicyclic monoterpene-based compound, and the IUPAC name is 6,6-dimethyl-2-methylenebicyclo[3,1,1]heptan-3-ol. The structural formula is $C_{10}H_{16}O$, and the molecular weight is 152.2 g/mol. Pinocarveol is a transparent and light-yellow liquid which does not dissolve in water but dissolve in oil and ethanol. Pinocarveol is used as a flavoring agent, exhibits woody, cooling minty, and pine-like fragrances, and is known as a safe and edible substance, which is approved as an ingredient in flavor and fragrance agents by Flavor and Extract Manufacturers' Association (FEMA), Food and Drug Administration (FDA), Korea Food and Drug Administration (KFDA), European Community (EC), and Joint FAO/WHO Expert Committee on Food Additives (JECFA), and is industrially used for the purpose of taste and smell. However, the physiological activity of pinocarveol has not been reported up to this date.

According to an embodiment of the present invention, pinocarveol of the present invention is trans-pinocarveol. According to another embodiment of the present invention, pinocarveol of the present invention is (−)-trans-pinocarveol.

Pinocarveol of the present invention may be used in the form of a pharmaceutically acceptable salt, and as the salt, an acid-addition salt formed by a pharmaceutically acceptable free acid is useful. As the free acid, inorganic acids and organic acids may be used.

Specifically, a pharmaceutically acceptable salt of pinocarveol of the present invention may be selected from the group consisting of hydrochloride, bromate, sulfate, phosphate, citrate, acetate, trifluoroacetate, lactate, tartrate, maleate, fumarate, gluconate, methanesulfonate, glyconate, succinate, 4-toluenesulfonate, gluturonate, embonate, glutamate, and aspartate, but is not limited thereto, and thus includes all salts formed using various inorganic acids and organic acids that are conventionally used in the art. In addition, compounds of the present invention may exist in the form of a solvate (e.g., hydrate).

According to another aspect of the present invention, the present invention provides a pharmaceutical composition for preventing or treating a metabolic disease, including pinocarveol or a pharmaceutically acceptable salt thereof as an active ingredient, wherein the metabolic disease is selected from the group consisting of obesity, diabetes, dyslipidemia, fatty liver, and insulin resistance syndrome.

According to the present invention, it was confirmed that pinocarveol of the present invention reduces body weight and visceral fat, lowers lipid concentration in blood, improves liver function index in blood, lowers blood sugar level, as well as suppresses metabolic inflammatory responses. Accordingly, compounds of the present invention can be effectively used as efficiently preventive or treatment compositions for multilaterally ameliorating various metabolic diseases.

As used herein, the term "diabetes" refers to a chronic disease which is characterized by relative or complete lack of insulin causing glucose intolerance. Diabetes of the present invention includes all types of diabetes, for example, type 1 diabetes, type 2 diabetes, and genetic diabetes. Type 1 diabetes is an insulin-dependent diabetic disease mainly caused by the destruction of β cells. Type 2 diabetes is an insulin-independent diabetic disease caused by insufficient secretion of insulin after meal or by insulin resistance.

As used herein, the term "dyslipidemia" is a concept including hyperlipidemia and refers to an abnormal lipid condition exhibited as problems of metabolic abnormality of lipoproteins as well as hypercholesterolemia, hypertriglyceridemia, low HDL cholesterolemia, and the like due to an increase in blood fat level.

As used herein, the term "fatty liver" refers to a condition in which an excessive amount of fat is accumulated in a hepatocyte due to lipid metabolism disorder of the liver, which causes various diseases such as angina, myocardial infarction, stroke, arteriosclerosis, fatty liver, and pancreatitis.

As used herein, the term "insulin resistance" means that the function of insulin to lower blood sugar level is deteriorated so that cells cannot effectively burn glucose. When insulin resistance is high, the body produces an excessive amount of insulin, and as a result, high blood pressure and dyslipidemia, as well as heart diseases, diabetes, and the like, may occur. In particular, in the case of type 2 diabetes, increases in the level of insulin in muscles and adipose tissues are not detected, thereby insulin is not activated.

As used herein, the term "insulin resistance syndrome" refers to a collective concept of diseases caused by the insulin resistance, refers to diseases characterized by cellular resistance against insulin actions, hyperinsulinemia, and increases in very low density lipoprotein (VLDL) and neutral fat, a decrease in high density lipoprotein (HDL), high blood pressure, and the like, and is a concept of being recognized as a risk factor of cardiovascular diseases and type 2 diabetes (Reaven G M, *Diabetes,* 37: 1595-607, (1988)). In addition, insulin resistance increases oxidative stress in cells along with risk factors such as high blood pressure, diabetes, smoking, and the like, and changes the signal transduction system to cause inflammatory responses, thereby leading to atherosclerosis (Freeman B A, et al., *Lab Invest* 47: 412-26, (1982), Kawamura M, et al., *J Clin Invest* 94: 771-8, (1994)).

As used herein, the term "metabolic disease" conceptualizes a phenomenon of various risk factors of cardiovascular diseases and type 2 diabetes that form groups into one disease group, and is a concept which collectively includes insulin resistance and various other complex metabolic abnormalities and clinical symptoms related thereto. In 1988, Reaven argued that the common cause of such symptoms is insulin resistance in which in vivo insulin action does not effectively function and named this phenomenon as insulin resistance syndrome, but in 1998, World Health Organization (WHO) introduced the term "metabolic syndrome" or "metabolic disease" because insulin resistance cannot explain all factors of such symptoms.

According to an embodiment of the present invention, dyslipidemia which is treated or prevented by the composition of the present invention is hyperlipidemia.

As used herein, the term "hyperlipidemia" refers to a disease caused by a high fat content in the blood because the metabolism of lipids such as neutral fat, cholesterol, and the like is not effectively carried out. More specifically, hyperlipidemia includes hypercholesterolemia or hypertriglyceridemia with a high frequency of occurrence due to conditions of the increased contents of neutral fat, LDL cholesterol, phosphatides, free fatty acids, and the like in the blood.

According to an embodiment of the present invention, fatty liver which can be treated or prevented by the composition of the present invention is non-alcoholic fatty liver.

As used herein, the term "non-alcoholic fatty liver (NAFL)" refers to a disease in which an excessive amount of fat is accumulated in hepatocytes regardless of absorption of excessive amount of alcohol.

According to an embodiment of the present invention, the composition of the present invention reduces body weight or diet efficiency. According to another embodiment of the present invention, the composition of the present invention reduces body weight or diet efficiency by 10%, 20%, or 30% or more. According to still another embodiment of the present invention, the composition of the present invention reduces body weight or diet efficiency by 10 to 60%, 20 to 60%, 30 to 60%, 10 to 50%, 20 to 50%, 30 to 50%, 10 to 40%, 20 to 40%, or 30 to 40%. As shown by the examples below, it was confirmed that a cumulative weight gain was decreased by 32% and diet efficiency was decreased by 32% in a group (PD) supplemented with pinocarveol compared to a high fat diet (HFD) control group (FIGS. 1A to 1D).

According to an embodiment of the present invention, the composition of the present invention reduces visceral fat. According to another embodiment of the present invention, the composition of the present invention reduces visceral fat by 10%, 20%, or 30% or more. According to a specific embodiment of the present invention, the composition of the present invention reduces visceral fat by 10 to 60%, 20 to 60%, 30 to 60%, 10 to 50%, 20 to 50%, 30 to 50%, 10 to 40%, 20 to 40%, or 30 to 40%. As shown by the examples below, it was confirmed that a visceral fat weight was decreased by 32% in the group (PD) supplemented with pinocarveol compared to the high fat diet (HFD) control group (FIGS. 2A to 2B). According to another embodiment of the present invention, visceral fat of the present invention is one or more fat selected from the group consisting of epididymal fat, fat around the kidney, mesenteric fat, and retroperitoneal fat.

Therefore, according to the present invention, it was confirmed that since the composition of the present invention significantly reduces weight, diet efficiency, and visceral fat compared to the high fat diet control group, the composition of the present invention exhibits an effect of preventing, ameliorating, or treating obesity.

As used herein, the terms "liver" and "internal organs" include cells or tissues, respectively.

According to an embodiment of the present invention, the composition of the present invention reduces plasma lipid concentrations. According to another embodiment of the present invention, plasma lipid of the present invention is a plasma lipid selected from the group consisting of neutral fat, all cholesterols, and free fatty acids. According to still another embodiment of the present invention, the composition of the present invention reduces a plasma lipid concentration by 10%, 20%, or 30% or more. According to a specific embodiment of the present invention, the composition of the present invention reduces visceral fat by 10 to 60%, 20 to 60%, 30 to 60%, 10 to 50%, 20 to 50%, 30 to 50%, 10 to 40%, 20 to 40%, 30 to 40%, 10 to 30%, 20 to 30%, or 10 to 20%. As shown by the examples below, it was confirmed that a neutral fat concentration was significantly decreased by 27%, a total cholesterol concentration was significantly decreased by 16%, and a free fatty acid concentration was significantly decreased by 39% in the group (PD) supplemented with pinocarveol compared to the high fat diet (HFD) control group (FIGS. 3A to 3D).

Therefore, according to the present invention, it was confirmed that since the composition of the present invention significantly reduces the plasma lipid concentration compared to the high fat diet control group, the composition of the present invention exhibits an effect of preventing, ameliorating, or treating dyslipidemia, more specifically, hyperlipidemia.

According to an embodiment of the present invention, the composition of the present invention reduces the weight of the liver or a lipid concentration in a hepatic tissue. According to another embodiment of the present invention, the composition of the present invention reduces the weight of the liver or a lipid concentration in a hepatic tissue by 10%, 20%, 30%, 40%, 50%, or 60% or more. According to a certain embodiment of the present invention, the composition of the present invention reduces the weight of the liver or a lipid concentration in a hepatic tissue by 10 to 80%, 20 to 80%, 30 to 80%, 40 to 80%, 50 to 80%, 60 to 80%, 10 to 70%, 20 to 70%, 30 to 70%, 40 to 70%, 50 to 70%, 60 to 70%, 10 to 60%, 20 to 60%, 30 to 60%, 10 to 50%, 20 to 50%, 30 to 50%, 10 to 40%, 20 to 40%, or 30 to 40%. According to another embodiment of the present invention, the lipid in a hepatic tissue of the present invention is a lipid selected from the group consisting of neutral fat, cholesterol, and free fatty acid. As shown by the examples below, it was confirmed that the weight of the liver was significantly decreased by 30%, a concentration of neutral fat in a hepatic tissue was significantly decreased by 33%, a cholesterol concentration in a hepatic tissue was significantly decreased by 31%, and a free fatty acid concentration in a hepatic tissue was significantly decreased by 65% in the group (PD) supplemented with pinocarveol compared to the high fat diet (HFD) control group (FIGS. 4A to 4E).

According to an embodiment of the present invention, the composition of the present invention reduces alanine aminotransferase (ALT) activity or aspartate aminotransferase (AST) activity in the blood. According to another embodiment of the present invention, the composition of the present invention reduces the amount of ALT by 10%, 20%, 30%, or 40% or more. According to a certain embodiment of the present invention, the composition of the present invention reduces the amount of ALT by 10 to 70%, 20 to 70%, 30 to 70%, 40 to 70%, 10 to 60%, 20 to 60%, 30 to 60%, 40 to 60%, 10 to 50%, 20 to 50%, 30 to 50%, or 40 to 50%. According to another embodiment of the present invention, the composition of the present invention decreases the amount of AST by 10%, 20%, or 30% or more. According to a certain embodiment of the present invention, the composition of the present invention decreases the amount of AST by 10 to 60%, 20 to 60%, 30 to 60%, 10 to 50%, 20 to 50%, 30 to 50%, 10 to 40%, 20 to 40%, or 30 to 40%. As shown by the examples below, it was confirmed that ALT was significantly decreased by 52%, and AST was significantly decreased by 34% in the group (PD) supplemented with pinocarveol compared to the high fat diet (HFD) control group (FIGS. 4F and 4G).

According to the present invention, it was confirmed that since the composition of the present invention significantly reduces the weight of the liver, the lipid concentration in a hepatic tissue, and the amounts of ALT and AST in blood compared to the high fat diet control group, the composition of the present invention exhibits an effect of preventing, ameliorating, or treating fatty liver, more specifically, non-alcoholic fatty liver.

According to an embodiment of the present invention, the composition of the present invention reduces a fasting blood sugar concentration or a fasting insulin concentration in blood. According to another embodiment of the present invention, the composition of the present invention reduces a fasting blood sugar concentration or a fasting insulin concentration in blood by 10%, 20%, 30%, 40%, or 50% or more. According to a certain embodiment of the present invention, the composition of the present invention reduces a fasting blood sugar concentration or a fasting insulin concentration in blood by 10 to 70%, 20 to 70%, 30 to 70%, 40 to 70%, 50 to 70%, 10 to 60%, 20 to 60%, 30 to 60%, 40 to 60%, 50 to 60%, 10 to 50%, 20 to 50%, 10 to 40%, 20 to 40%, 10 to 30%, or 20 to 30%. As shown by the examples below, it was confirmed that the fasting blood sugar concentration was significantly decreased by 21%, and the fasting insulin concentration in blood was significantly decreased by 50% in the group (PD) supplemented with pinocarveol compared to the high fat diet (HFD) control group (FIGS. 5A to 5D).

According to the present invention, it was confirmed that since the composition of the present invention significantly reduces the fasting blood sugar concentration or the fasting insulin concentration in blood compared to the high fat diet control group, the composition of the present invention exhibits an effect of preventing, ameliorating, or treating diabetes more specifically, type 2 diabetes.

According to an embodiment of the present invention, the composition of the present invention reduces an inflammatory cytokine concentration in blood. According to another embodiment of the present invention, the composition of the present invention reduces an inflammatory cytokine concentration in blood by 10%, 20%, 30%, 40%, 50%, 60%, or 70% or more. According to a certain embodiment of the present invention, the composition of the present invention reduces an inflammatory cytokine concentration in blood by 10 to 90%, 20 to 90%, 30 to 90%, 40 to 90%, 50 to 90%, 60 to 90%, 70 to 90%, 10 to 80%, 20 to 80%, 30 to 80%, 40 to 80%, 50 to 80%, 60 to 80%, 70 to 80%, 10 to 60%, 20 to 60%, 30 to 60%, 40 to 60%, 10 to 50%, 20 to 50%, 30 to 50%, 40 to 50%, 10 to 40%, 20 to 40%, 30 to 40%, 10 to 30%, or 20 to 30%. According to another embodiment of the present invention, the inflammatory cytokine in blood of the present invention is a cytokine selected from the group consisting of IL-6, TNFα, MCP1, and leptin. As shown by the examples below, it was confirmed that the amount of IL-6 was significantly decreased by 70%, the amount of TNFα was significantly decreased by 28%, the amount of MCP1 was significantly decreased by 35%, and the amount of leptin was significantly decreased by 40% in the group (PD) supplemented with pinocarveol compared to the high fat diet (HFD) control group (FIGS. 6A-6D). According to the present invention, it was confirmed that since the composition of the present invention significantly reduces the inflammatory cytokine concentration in blood compared to the high fat diet control group, the composition of the present invention exhibits an effect of preventing, ameliorating, or treating inflammation activation induced by obesity.

According to an embodiment of the present invention, the composition of the present invention increases expression of uncoupling protein 1 (UCP1), uncoupling protein 3 (UCP3), peroxisome proliferator-activated receptor-gamma coactivator 1 alpha (PGC-1α), or β-catenin, or activation of AMP-activated protein kinase (AMPK); or reduces expression of CCAAT enhancer-binding proteins (C/EBPα), peroxisome proliferator-activated receptor gamma (PPARγ), cluster of differentiation 36 (CD36), fatty acid synthase (FAS), leptin, sterol regulatory element-binding factor 1c (SREBP1C), liver X receptor alpha (LXRα), lipoprotein lipase (LPL), or acetyl-CoA carboxylase (ACC), in visceral fat or the liver. As shown by the following examples, in the case of the HFD group, expressions of genes related to thermogenesis (i.e., UCP1, UCP3, and PGC-1α) were all significantly decreased compared to the normal diet group, but in the PD group, expressions of the genes which were reduced due to an intake of high fat diet were significantly increased again (FIG. 7A). In addition, in the case of the HFD group, expressions of C/EBPα, PPARγ2, CD36, FAS, and leptin which are involved in adipogenesis were all significantly increased compared to the normal diet group, but in the PD group, expressions of the genes which were increased due to an intake of high fat diet were significantly decreased again (FIG. 7B). Moreover, an expression amount of β-catenin protein which is an upstream signal transduction substance controlling lipogenesis was significantly increased in the PD group compared to the HFD group (FIG. 7C). In addition, in the case of the HFD group, expressions of SREBP, LXRα, LPL, FAS, and ACC which are important in lipogenesis were all significantly increased compared to the normal diet group, but in the case of the PD group, expressions thereof all were significantly decreased again (FIG. 8A), and activation (p-AMPK/AMPK ratio) of AMPK which is a signal transduction substance promoting oxidation of fatty acids was significantly increased (FIG. 8B). Therefore, according to the present invention, the composition of the present invention reduces gene expressions of nuclear transcription factors and the targets thereof which play a pivotal role in the lipogenesis in visceral adipose tissues, and increases the protein expression of β-catenin, thereby exhibiting effects of preventing, ameliorating, or treating accumulation of visceral fat. In addition, the composition of the present invention reduces gene expressions of nuclear transcription factors and the targets thereof which play a pivotal role in the lipogenesis in hepatic tissues, and increases activation of signal transduction substances that promote oxidation of fatty acids, thereby exhibiting an effect of preventing, ameliorating, or treating fatty liver induced by obesity.

In cases where the composition of the present invention is prepared as a pharmaceutical composition, the pharmaceutical composition of the present invention contains a pharmaceutically acceptable carrier. The pharmaceutically acceptable carrier contained in the pharmaceutical composition of the present invention is one that is conventionally used for the formulation, and examples thereof may include lactose, dextrose, sucrose, sorbitol, starch, acacia gum, calciumphosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil, but the present invention is not limited thereto. The pharmaceutical composition of the present invention may further contain, in addition to the above ingredients, a lubricant, a wetting agent, a sweetening agent, a flavoring agent, an emulsifier, a suspending agent, a preservative, and the like. Suitable pharmaceutically acceptable carriers and agents are described in detail in *Remington's Pharmaceutical Sciences* (19th ed., 1995).

The pharmaceutical composition of the present invention may be administered orally or parenterally, and examples of parenteral administration may include intravenous, subcutaneous, intramuscular, intraperitoneal, transdermal injections, and the like. Specifically, the pharmaceutical composition of the present invention may be orally administered.

A suitable administration dose of the pharmaceutical composition of the present invention may vary depending on various factors, such as method of formulation, manner of administration, age, body weight, sex, and morbidity of the patient, diet, administration time, route of administration, excretion rate, and response sensitivity. The dose per day of the pharmaceutical composition of the present invention may be, for example, 0.0001 to 1,000 mg/kg.

The pharmaceutical composition of the present invention may be formulated into a unit dose or by inserting into a multi-dose container, using the pharmaceutically acceptable carriers and/or excipients according to the methods known to those skilled in the art. At this time, the dosage form may be in the form of oil or a solution in an aqueous medium, suspension, syrup, or emulsion, or in the form of an excipient, powder, fine powder, granule, tablet, or capsule, and a dispersant or stabilizer may be additionally included.

According to another aspect of the present invention, the present invention provides a functional food composition for preventing or ameliorating a metabolic disease, including pinocarveol of the present invention as an active ingredient, wherein the metabolic disease is selected from the group consisting of obesity, diabetes, dyslipidemia, fatty liver, and insulin resistance syndrome.

According to another aspect of the present invention, the present invention provides a food composition for preventing or ameliorating a metabolic disease, including pinocarveol of the present invention as an active ingredient, wherein the metabolic disease is selected from the group consisting of obesity, diabetes, dyslipidemia, fatty liver, and insulin resistance syndrome.

Since the functional food composition or food composition of the present invention has a common active ingredient (i.e., pinocarveol) with the pharmaceutical composition described above, the description of the overlapping content in the relationship with the pharmaceutical composition is omitted to avoid excessive complexity of the present invention.

When the composition of the present invention is prepared as a functional food composition or a food composition, ingredients that are conventionally added in the preparation of functional foods or foods, for example, proteins, carbohydrates, fats, nutrients, seasoning agents, and flavoring agents, as well as pinocarveol of the present invention are included as active ingredients. The carbohydrates described above may include monosaccharides (e.g., glucose, fructose, etc.); disaccharides (e.g., maltose, sucrose, etc.); oligosaccharides; polysaccharides (e.g., dextrin, cyclodextrin, etc.); and sugar alcohols (e.g., xylitol, sorbitol, erythritol, etc.). As flavoring agents, natural flavoring agents (thaumatin and stevia extracts (e.g., rebaudioside A, glycyrrhizin, etc.) and synthetic flavoring agents (saccharine, aspartame, etc.) may be used.

For example, when the functional food composition or the food composition of the present invention is prepared as a health drink, in addition to pinocarveol which is an active ingredient of the present invention, citric acid, high fructose corn syrup, sugar, glucose, acetic acid, malic acid, fruit juice, eucommia bark extract, jujube extract, licorice juice, or the like may be additionally included.

Since the compositions of the present invention have a common active ingredient of a plant including pinocarveol described above as a main ingredient, the description of the overlapping content in the relationship with the composition including pinocarveol as an active ingredient is omitted to avoid excessive complexity of the present invention.

According to still another aspect of the present invention, the present invention provides a method of preventing or treating a metabolic disease, including administering a pharmaceutical composition including pinocarveol as an active ingredient to a subject in need thereof, wherein the metabolic disease is selected from the group consisting of obesity, diabetes, dyslipidemia, fatty liver, and insulin resistance syndrome.

In an embodiment of the present invention, dyslipidemia of the present invention is hyperlipidemia.

In another embodiment of the present invention, fatty liver of the present invention is non-alcoholic fatty liver.

Since the method of preventing or treating a metabolic disease of the present invention is related to a method using the pharmaceutical composition for preventing or treating a metabolic disease as another aspect of the present invention, the description of the overlapping content is omitted to avoid excessive complexity of the present invention.

The characteristics and advantages of the present invention are summarized as follows:

(a) The present invention provides a pharmaceutical composition for preventing or treating a metabolic disease including pinocarveol as an active ingredient and a functional food composition for preventing or ameliorating a metabolic disease using the same.

(b) Pinocarveol of the present invention reduces body weight and visceral fat, lowers a lipid concentration in blood, improves liver function index in blood, lowers blood glucose level, and suppresses metabolic inflammatory responses, so as to be effectively used as a pharmaceutical or functional food composition exhibiting a preventive or treatment activity for a metabolic disease selected from the group consisting of obesity, diabetes, dyslipidemia, fatty liver, and insulin resistance syndrome.

DETAILED DESCRIPTION OF THE INVENTION

Figure 1A:
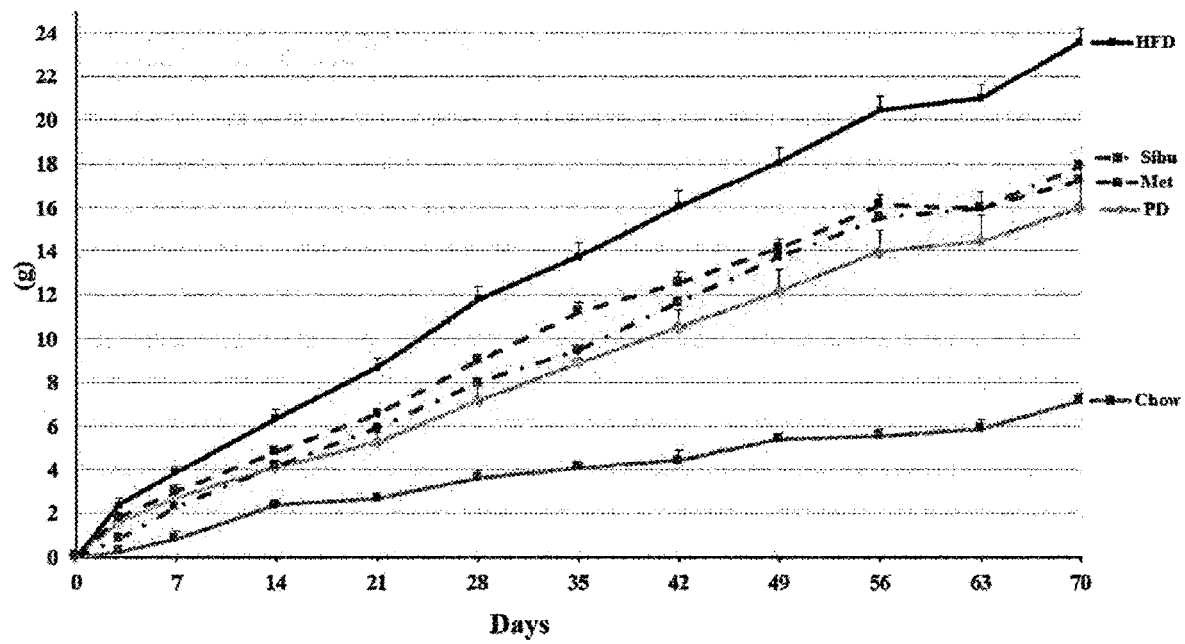
FIGS. 1A-1D shows an increased amount of weight of mice fed within experimental diet (FIG. 1A) and a diet intake amount thereof (FIG. 1B-1D). Each value is a mean±standard deviation (SEM) of the measurement values of 8 mice. The letter on the graph bar indicates a significant difference within $P<0.001$ according to one-way ANOVA analysis and Duncan's multiple range test.

Hereinafter, exemplary embodiments of the present invention will be described in detail. However, these exemplary embodiments are only for more specifically describing the present invention, and it will be apparent to those of ordinary skill in the art that the scope of the present invention is not limited by these exemplary embodiments in accordance with the gist of the present invention.

EXAMPLES

Example 1: Effect of Pinocarveol on Reduction of Body Weight and Visceral Fat in Dietary Obese Mice 1) Preparation of Experimental Diets and Raising of Experimental Animals An obesity inducing diet used in the present invention included a high fat control diet (HFD: 40% fat calorie, 17 g lard, and 3% corn oil/100 g diet), and a pinocarveol-supplemented high fat diet (PD) supplemented with pinocarveol (80,613, Sigma-Aldrich Company, CAS Number: 547-61-5, (1S,3R,5S)-6,6-dimethyl-2-methylenebicyclo[3,1,1]heptan-3-ol) has the same composition as HFD, but about 0.2% of pinocarveol was added. As a control drug, metformin (Met) or sibutramine (Sibu) which is an anti-obesity drug was added at a concentration of about 0.01% to HFD and used (Table 1). For a normal diet (chow) group, a commercially available rodent chow was fed. Pinocarveol, metformin, and sibutramine were all purchased from Sigma-Aldrich Company (U.S.).

TABLE 1

Experimental diet composition table (g/kg diet)

| Ingredient | High fat diet (HFD) control | Pinocarveol-supplemented diet (PD) | Metformin-supplemented diet (Met) | Sibutramine-supplemented diet (Sibu) |
| --- | --- | --- | --- | --- |
| Casein | 200 | 200 | 200 | 200 |
| DL-Methionine | 3 | 3 | 3 | 3 |
| Corn starch | 111 | 109 | 110 | 110.9 |
| Sucrose | 370 | 370 | 370 | 370 |
| Cellulose | 50 | 50 | 50 | 50 |
| Corn oil | 30 | 30 | 30 | 30 |
| Lard | 170 | 170 | 170 | 170 |
| Vitamin complex | 12 | 12 | 12 | 12 |
| Mineral complex | 42 | 42 | 42 | 42 |
| Choline bitartrate | 2 | 2 | 2 | 2 |
| Cholesterol | 10 | 10 | 10 | 10 |
| tert-Butylhydroquinone | 0.04 | 0.04 | 0.04 | 0.04 |
| Experimental substance | — | 2 | 1 | 0.1 |
| Total amount (g) | 1,000 | 1,000 | 1,000 | 1,000 |
| Fat (% calorie) | 39.0 | 39.0 | 39.0 | 39.0 |
| Total calorie, kJ/kg diet | 19,315 | 19,315 | 19,315 | 19,315 |

5-week-old male C57BL/6J mice (Orient, Korea) were adjusted to a laboratory condition with solid feed for one week and randomly assigned to a high fat diet control group and experimental groups according to the randomized block method, followed by raising for ten weeks. Diet was supplied with water between 10 and 11 a.m. every day, intake amounts of diet was measured every day, and weight was measured every week. In order to prevent sudden weight changes due to feed intake, feed containers were removed, and weight was measured after 2 hours. Experimental animals were fasted for 12 hours or longer and anaesthetized by diethyl ether, and blood, liver, adipose tissues of internal organs (epididymal fat, fat around the kidney, mesenteric fat, and retroperitoneal fat) were collected, washed with 0.1M phosphate buffer solution (pH 7.4), and measured for weight. Blood collected from abdominal aorta was centrifuged at 1,000×g for 15 minutes to separate blood plasma.

2) Changes in Body Weight and Visceral Fat Weight

Figure 1B:
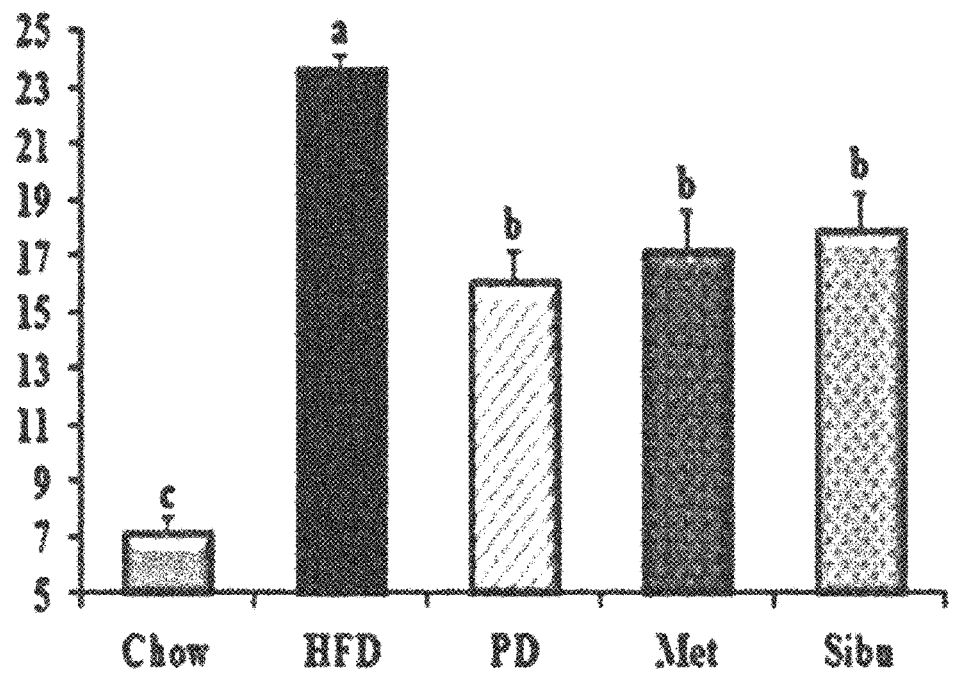
Figure 1C:
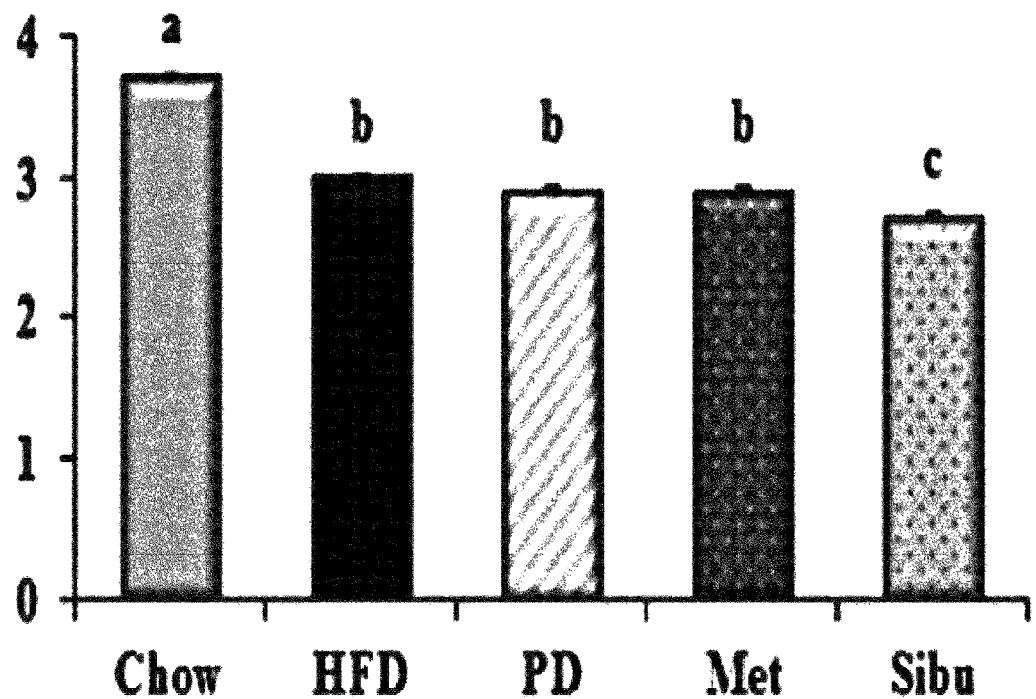
Figure 1D:
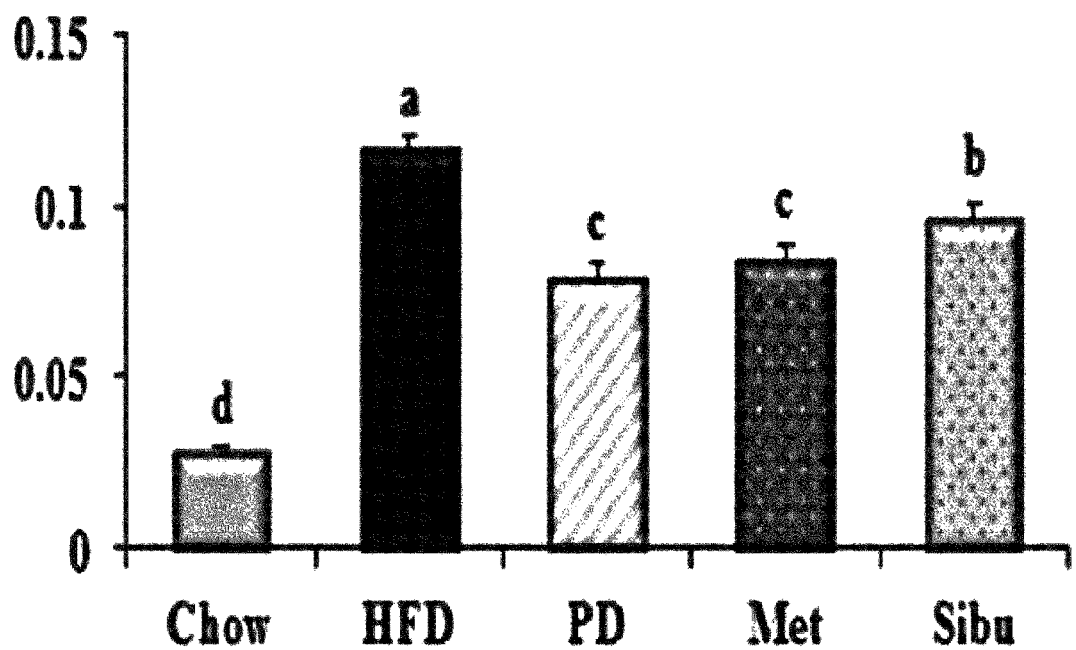

After feeding the experimental diets for 10 weeks, the final weight and the increased amount of body weight over 10 weeks were considered. Compared to the high fat diet control group (HFD), the pinocarveol-supplemented group (PD) showed a significant decrease of 32% in the cumulative body weight gain (FIGS. 1A and 1B). Pinocarveol intake did not cause any significant changes in daily diet intake amount, and as a result, the food efficiency ratio where the cumulative body weight gain is divided by the total diet intake amount during the experimental raising was also significantly decreased by 32% in the PD group compared to the HFD group (FIGS. 1C and 1D). As a result, it was found that the effect of reducing body weight of pinocarveol was not due to appetite suppression.

Figure 2A:
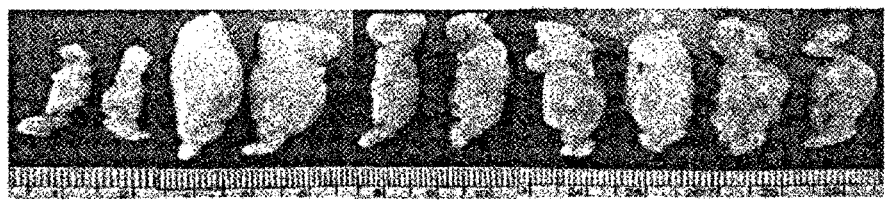
FIGS. 2A-2B shows images of visceral adipose tissues of mice fed with the experimental diet (FIG. 2A) and visceral fat weights for each part (FIG. 2B). Each value is a mean±standard deviation (SEM) of the measurement values of 8 mice. The letter on the graph bar indicates a significant difference within $P<0.001$ according to one-way ANOVA analysis and Duncan's multiple range test.
Figure 2A:
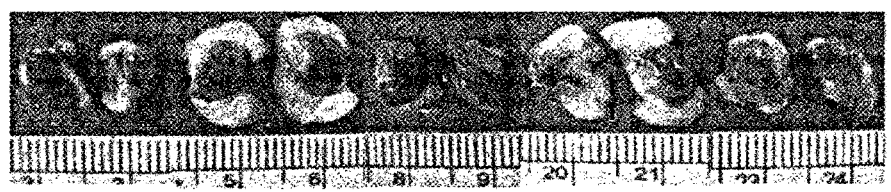
Figure 2A:
Figure 2A:
Figure 2B:
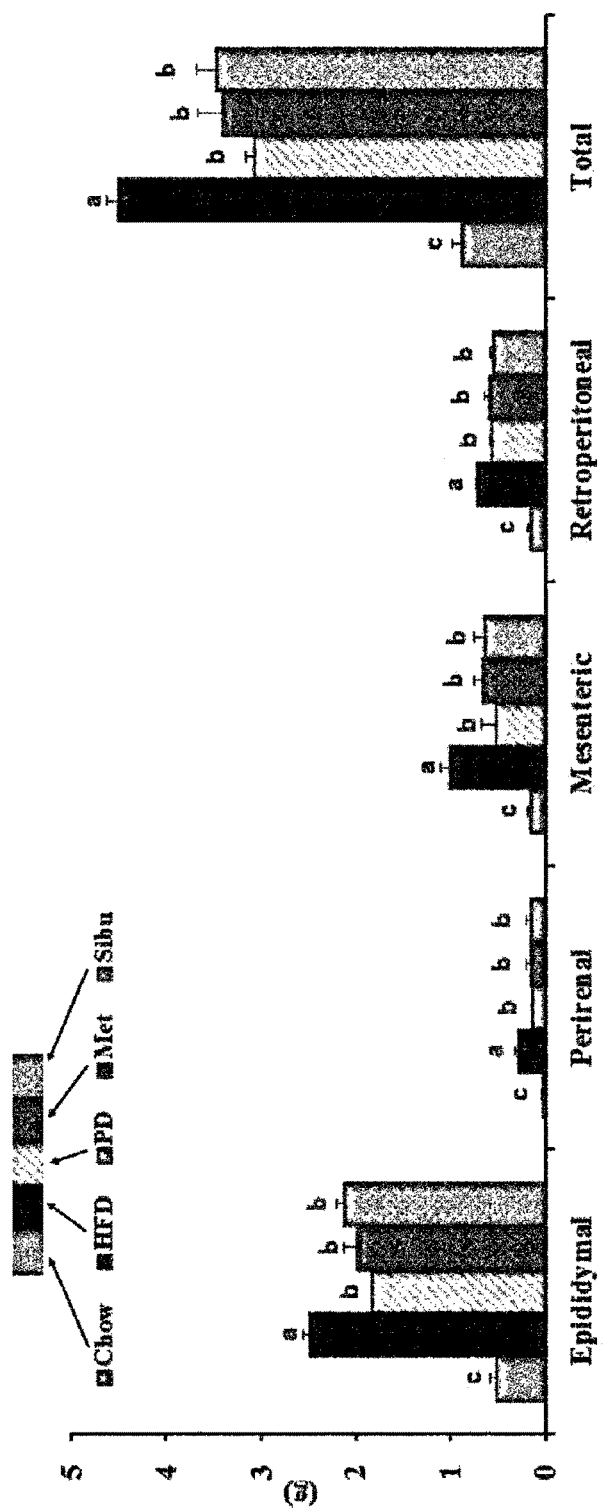
Figure 3A:
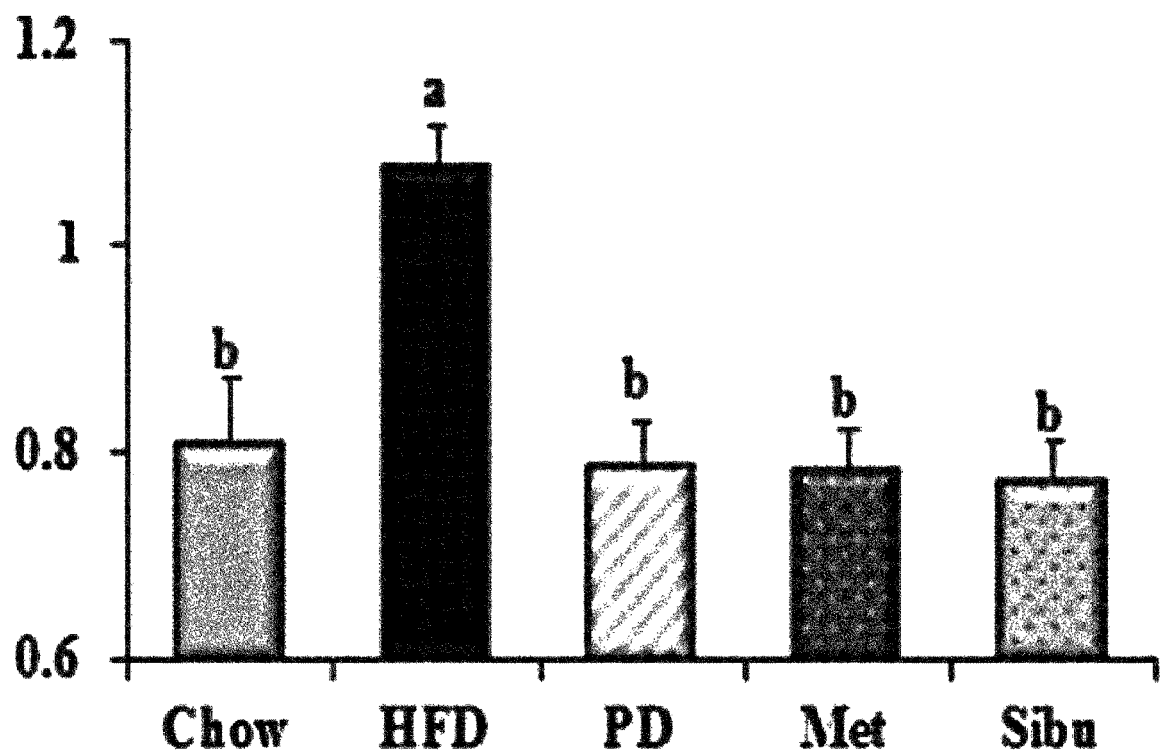
FIGS. 3A-3D shows lipid concentrations in blood of mice fed with the experimental diet (FIG. 3A: neutral fat (mmol/L), FIG. 3B: total cholesterol (mmol/L), FIG. 3C: HDL-cholesterol (mmol/L), and FIG. 3D: free fatty acid (μEq/L)). Each value is a mean±standard deviation (SEM) of the measurement values of 8 mice. The letter on the same column indicates a significant difference within $P<0.05$ according to one-way ANOVA analysis and Duncan's multiple range test.
Figure 3B:
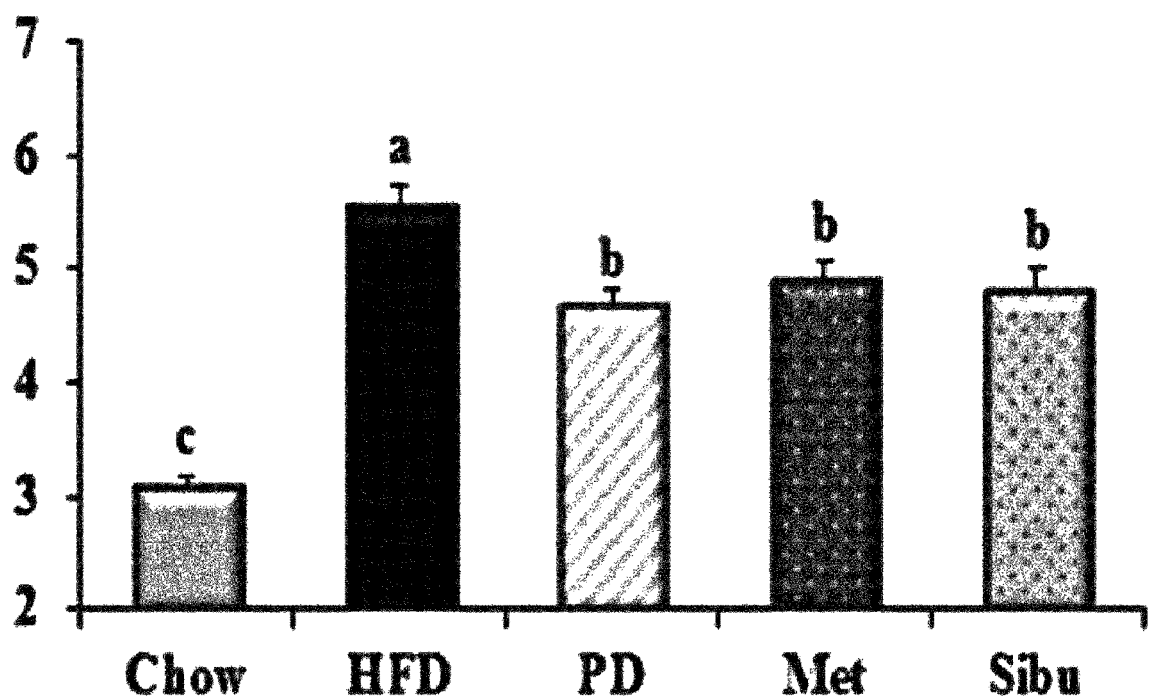
Figure 3C:
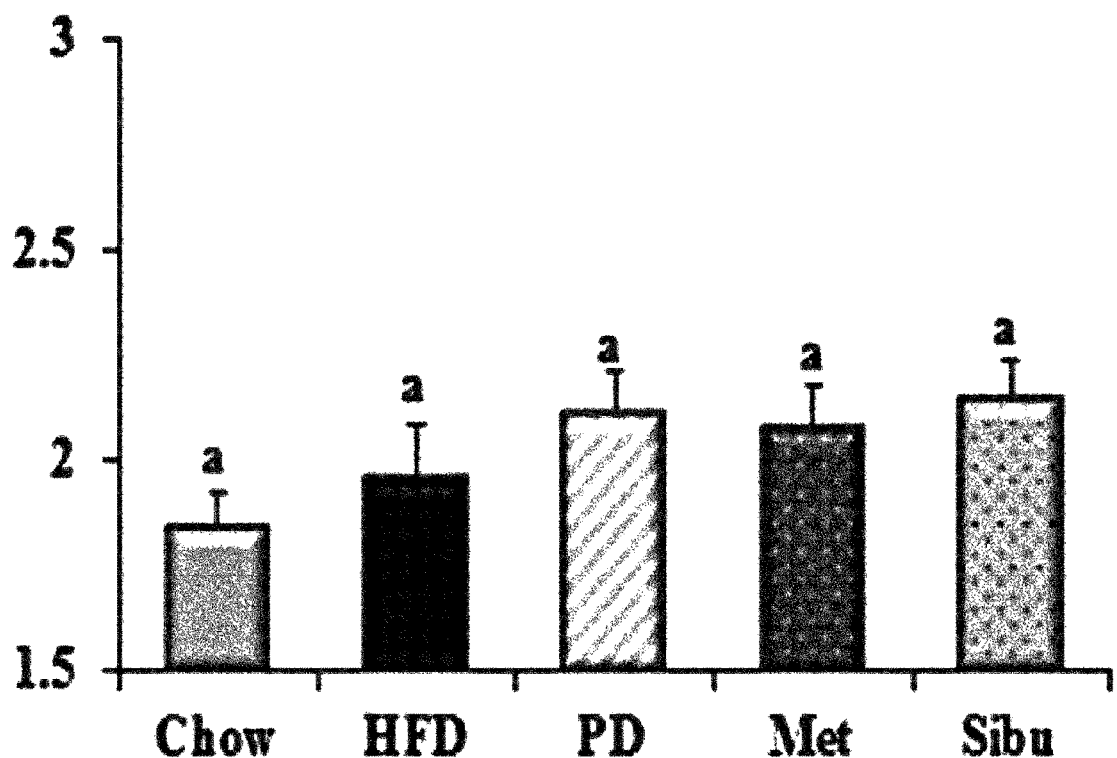
Figure 3D:
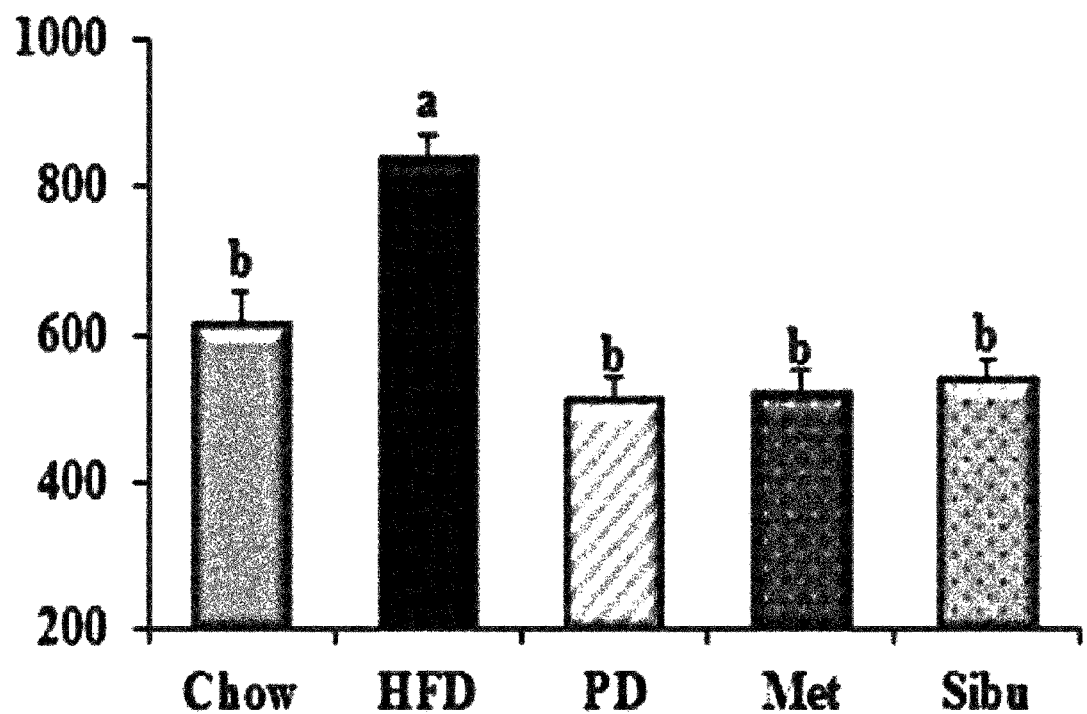

After feeding the experimental diets for 10 weeks, each of epididymal fat, fat around the kidney, mesenteric fat, and retroperitoneal fat, which compose visceral fat, was extracted to measure the weight thereof. As a result, in the pinocarveol-supplemented group (PD), the weights of epididymal fat, fat around the kidney, mesenteric fat, and retroperitoneal fat were significantly reduced compared to the control group (HFD), and the total visceral fat weight where the weights of the four parts are added was significantly reduced by 32% (FIG. 2B). Therefore, it was confirmed that pinocarveol exhibited as much excellent effect of reducing body weight and visceral fat amount as commercially available anti-obesity drugs (sibutramine) and diabetes treatment drugs (metformin).

Example 2: Effects of Pinocarveol on Preventing or Treating Hyperlipidemia of Dietary Obese Mice 1) Biochemical Analysis Method of Blood In order to evaluate the concentrations of plasma cholesterol, neutral fat, and free fatty acids of experimental animals raised for ten weeks, a commercially available measurement kit (Bio Clinical System, Korea) was used to perform measurement by repeating 2 measurements, respectively.

2) Changes in Plasma Lipid Concentration

Plasma lipid concentrations of mice fed with the experimental diet for ten weeks were considered. Compared to the HFD group, the PD group showed significant decreases of 27% in the neutral fat concentration, 16% in the total cholesterol concentration, and 39% in the free fatty acid concentration. Meanwhile, the HDL-cholesterol concentration in blood did not show any significant difference between the experimental groups (FIGS. 3A-3D). Therefore, pinocarveol exhibited an effect of significantly alleviating hyperlipidemia which is displayed in obesity induced by high fat diet, and such a hyperlipidemia improving effect is similar to or more excellent than the used control drugs (sibutramine and metformin).

Example 3: Effect of Pinocarveol for Preventing or Treating Non-Alcoholic Fatty Liver in Dietary Obese Mice 1) Analysis Method of Lipid Concentration in Hepatic Tissue Lipid components of hepatic tissues were collected as follows according to the method by Folch, et al. (Folch J, Lees M, Sloane Stanley G H. A simple method for the isolation and purification of total lipids from animal tissues. *J Bio Chem.* 1957; 226: 497-509). 1 mL of distilled water was applied to a hepatic tissue (0.25 g) and homogenized by using a Polytron homogenizer (IKA-WERKE GmbH & Co., Ultra-Turrax, Staufen, Germany). 5 mL of a chloroform: methanol solution (2:1, v/v) was added to the homogeneous solution, mixed well and centrifuged at 1,000×g for 10 minutes to separate a lower phase. 2 mL of a chloroform: methanol solution (2:1, v/v) was added to an upper phase again, and after repeating the same procedure, lipid components of the liver were completely separated. 3 mL of a chloroform:methanol:0.05% $CaCl_2$) (3:48:47, v/v/v) solution was added to the lower phase thus obtained, mixed for 1 minute, and centrifuged at 1,000×g for 10 minutes. After obtaining the final lower phase and completely drying with nitrogen gas, the dried lipids were dissolved in 1 mL of methanol to use for lipid component analysis.

The concentrations of neutral fat, cholesterol, and free fatty acids of the lipid extracts of hepatic tissues were measured by using the same commercially available measurement kit (Bio Clinical System, Korea) as previously used for the analysis of plasma lipid concentration.

2) Changes in Lipid Concentration of Hepatic Tissue and Liver Function Index

Figure 4A:
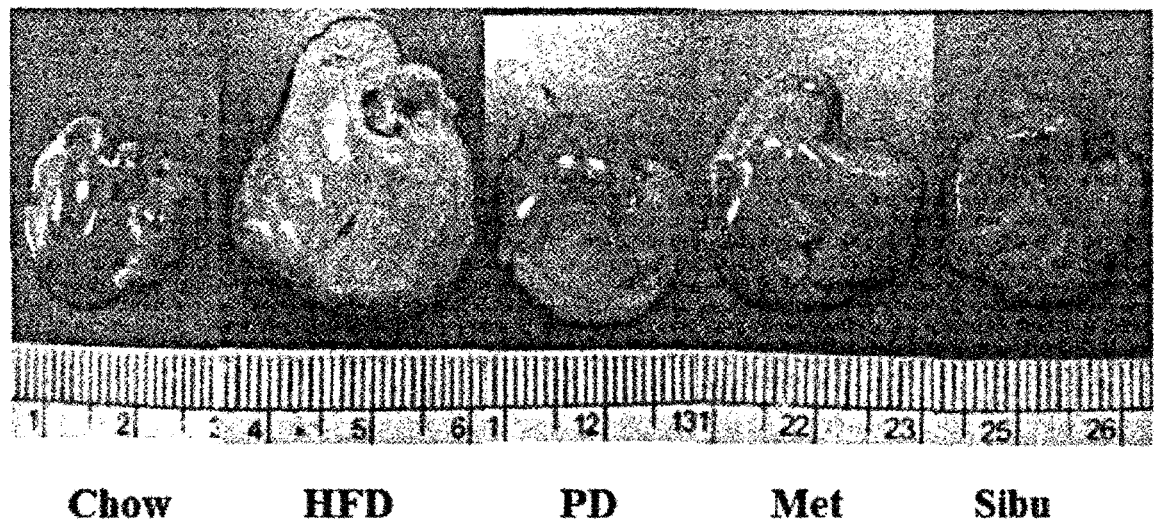
FIGS. 4A-4G shows indicators related to the non-alcoholic fatty liver of mice fed with the experimental diet (FIG. 4A: image of hepatic tissue, FIG. 4B: weight of liver (g), FIG. 4C: neutral fat (μmol/g), FIG. 4D: cholesterol (μmol/g), FIG. 4E: free fatty acid (μEq/g), FIG. 4F: alanineaminotransferase (IU/L), and FIG. 4G: aspartateaminotransferase (IU/L)). Each value is a mean±standard deviation (SEM) of the measurement values of 8 mice. The letter on the same column indicates a significant difference within $P<0.05$ according to one-way ANOVA analysis and Duncan's multiple range test.
Figure 4B:
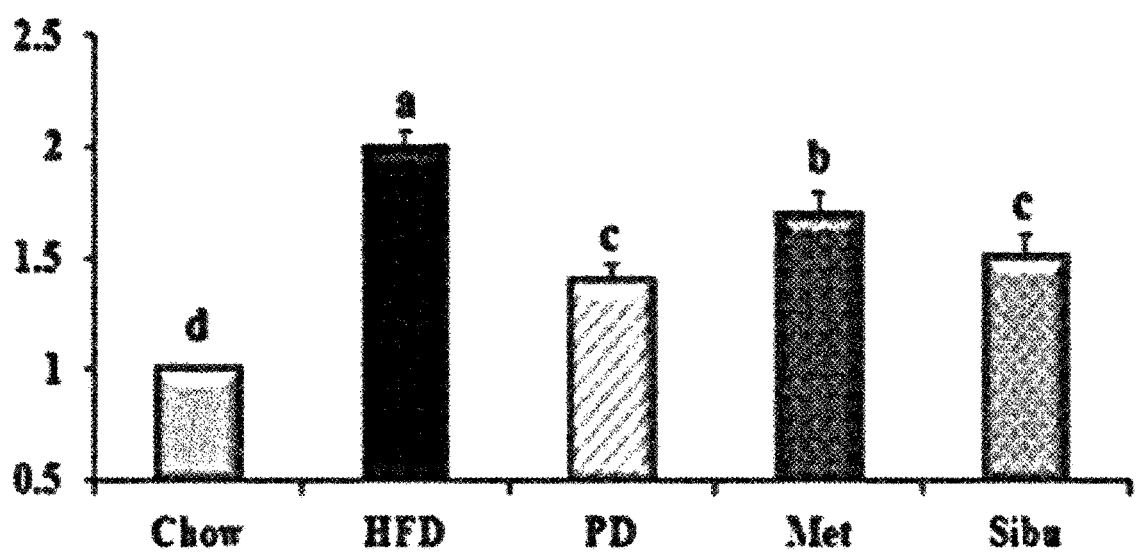

Weights of the liver of mice fed with the experimental diet for ten weeks were considered. Compared to the HFD group, the PD group showed significant decreases of 30% in the absolute liver weight (g) (FIGS. 4A and 4B).

Figure 4C:
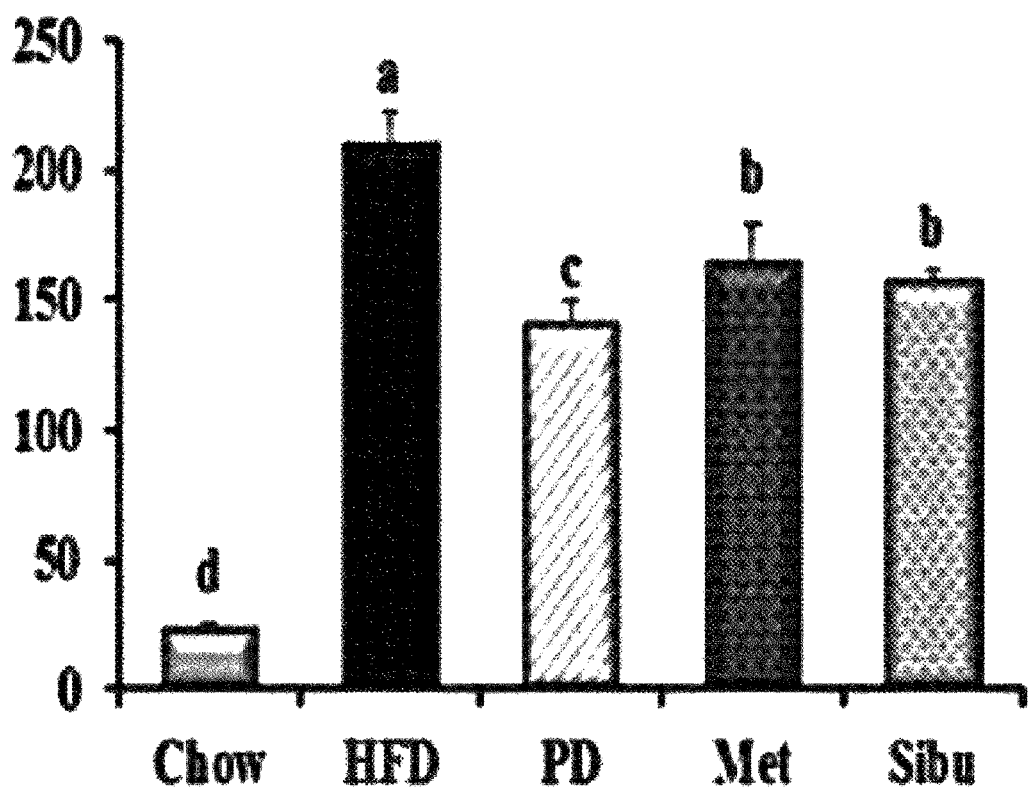
Figure 4D:
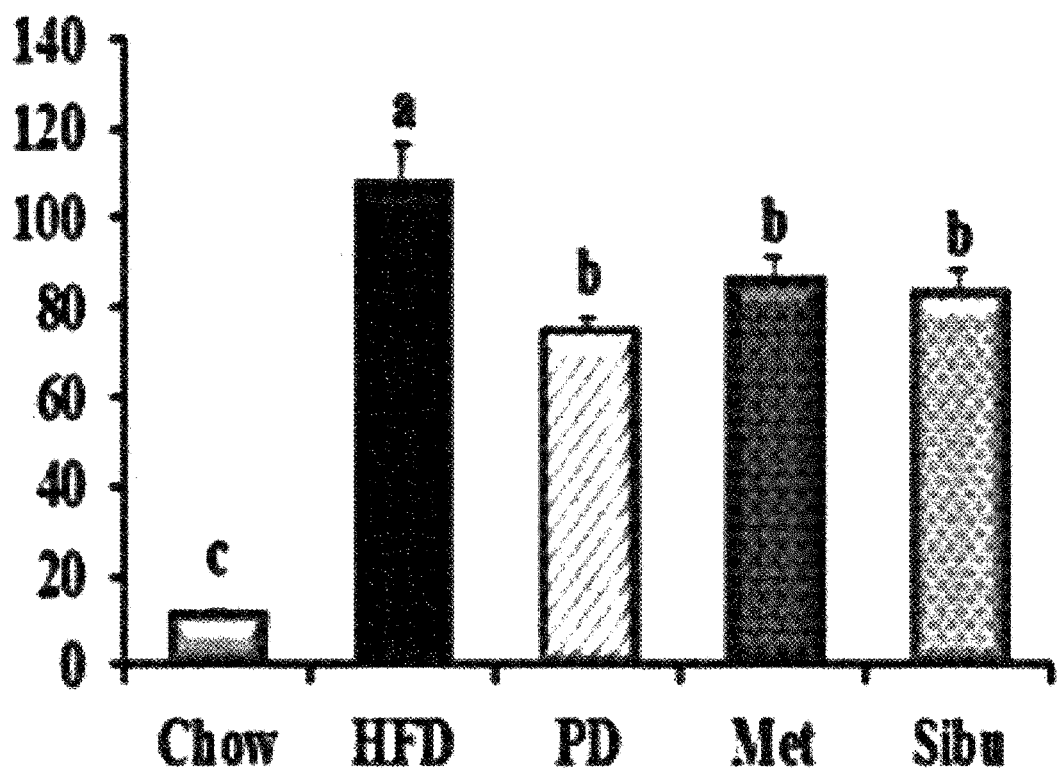
Figure 4E:
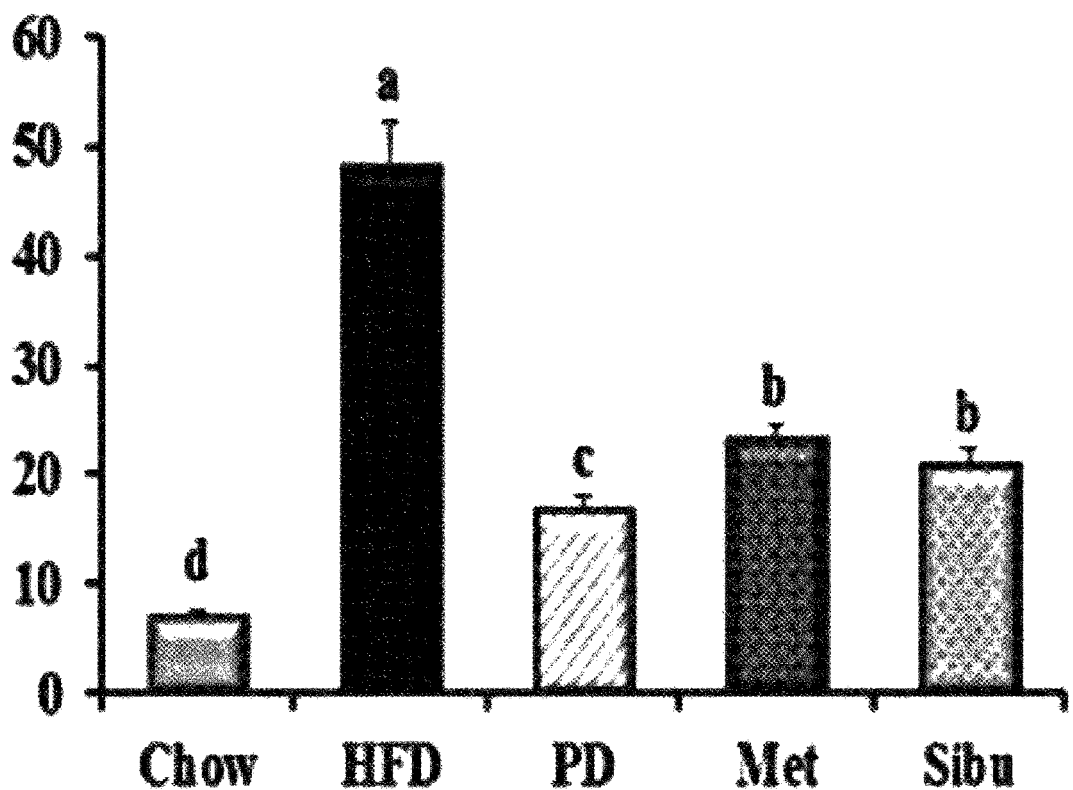
Figure 4F:
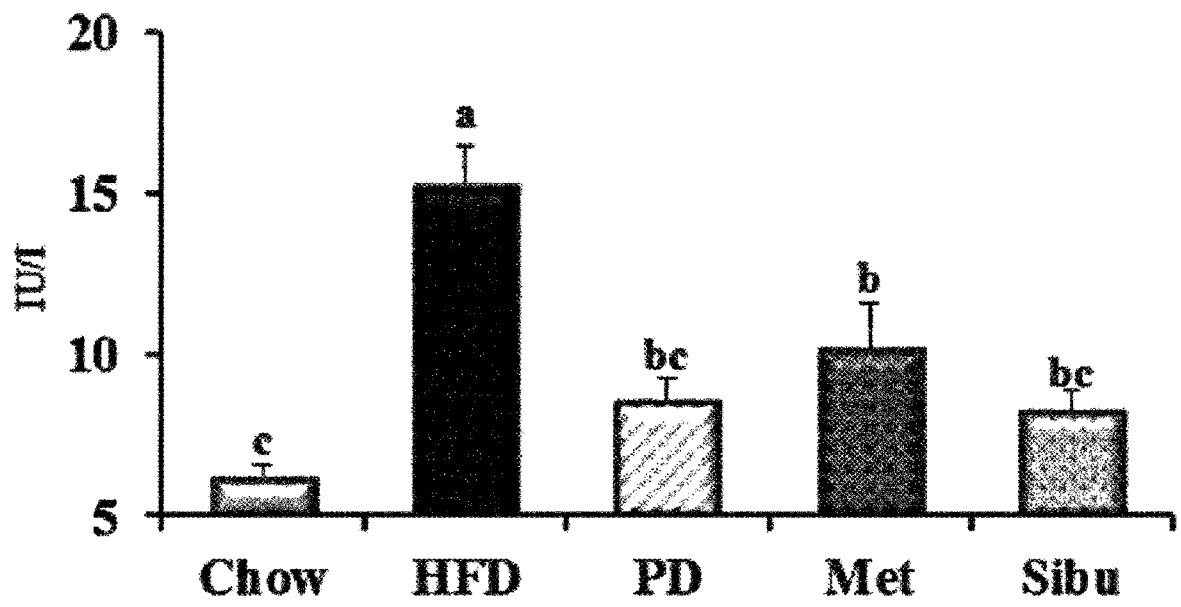
Figure 4G:
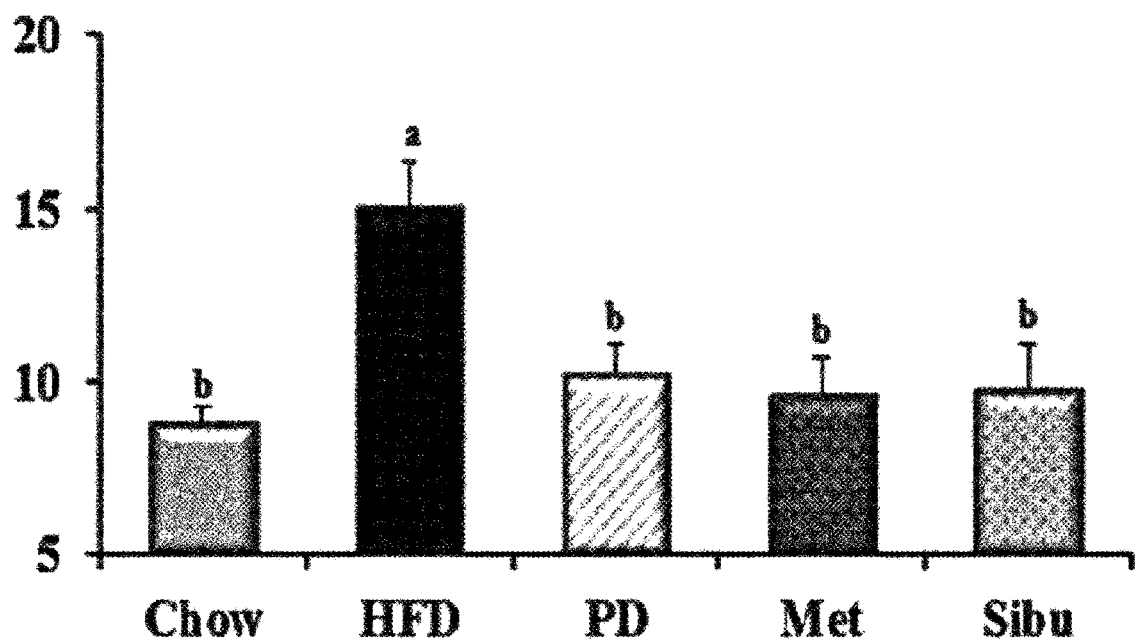

Lipid concentrations of hepatic tissues were considered. Compared to the HFD group, the PD group showed significant decreases of 33% in the neutral fat concentration, 31% in total cholesterol concentration, and 65% in the free fatty acid concentration (FIGS. 4C and 4D). Compared to the HFD group, the PD group showed significant decreases of 44% in the alanine aminotransferase (ALT) activity and 32% in the aspartate aminotransferase (AST) activity which are liver function indexes measured in blood plasma (FIGS. 4F and 4G). Therefore, pinocarveol exhibited an effect of significantly alleviating fatty liver phenomena which are displayed in obesity induced by high fat diet, and such a fatty liver improving effect of pinocarveol is similar to or more excellent than that of the control drugs.

Example 4: Effects of Pinocarveol on Preventing or Treating Type 2 Diabetes and Insulin Resistance Syndrome in Dietary Obese Mice 1) Oral Glucose Tolerance Test and Measurement Method of Blood Sugar and Insulin Concentrations During Fasting At 8 weeks of experimental raising, experimental animals were fasted for 16 hours and orally administered with d-glucose corresponding to 2 g/kg body weight, and blood was collected from the tail vein of mice at time points of 15 minutes, 30 minutes, 60 minutes, and 120 minutes. The glucose concentration of collected blood was measured by using a script-operation blood glucose sensor (ONETOUCH Ultra, Inverness Medical Ltd., U.K.).

Meanwhile, the glucose concentration of the blood plasma obtained during fasting which was collected from mice raised for 10 weeks was measured by using a biochemical automatic analyzer (Express Plus, Chiron Diagnostics Co., U.S.), and kit reagents for analysis were purchased from Bio-Clinical System (Korea).

The insulin concentration of blood plasma obtained during fasting was measured by using a mouse insulin ELISA kit (Millipore Corporation, U.S.).

Figure 5A:
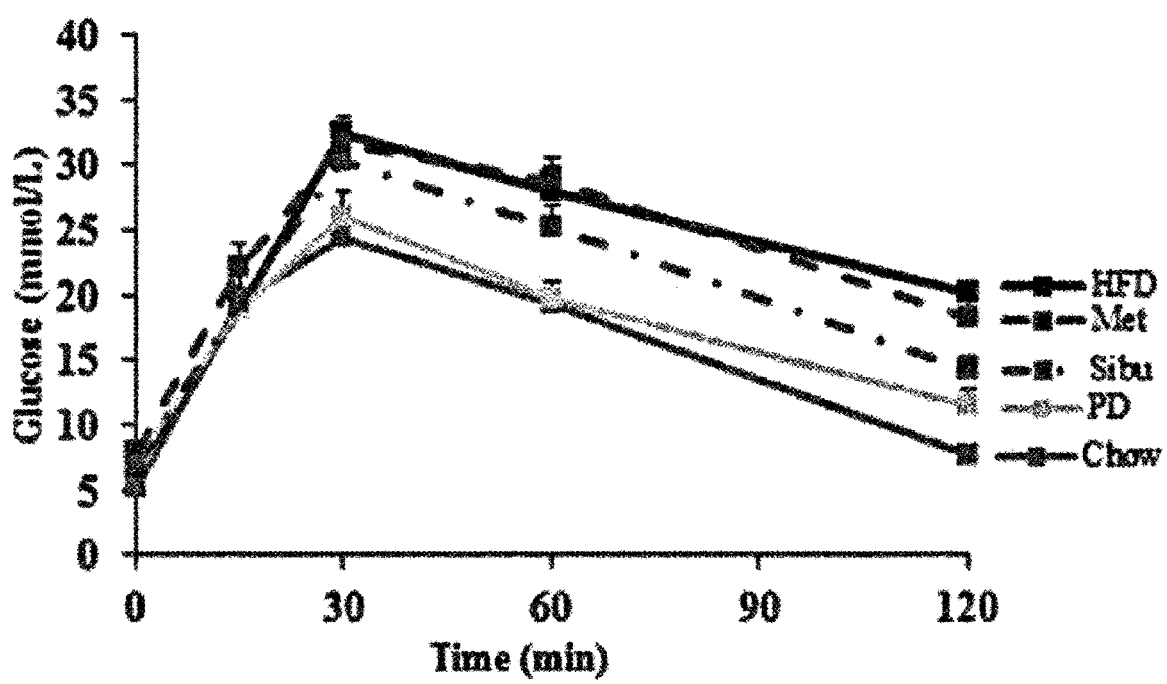
FIGS. 5A-5D shows indicators related to the insulin resistance of mice fed with the experimental diet (FIG. 5A: oral glucose tolerance test, FIG. 5B: AUC, FIG. 5C: blood glucose level during fasting (mmol/L), and FIG. 5D: insulin level during fasting (pg/mL)). The letter on the same column indicates a significant difference within $P<0.05$ according to one-way ANOVA analysis and Duncan's multiple range test.
Figure 5B:
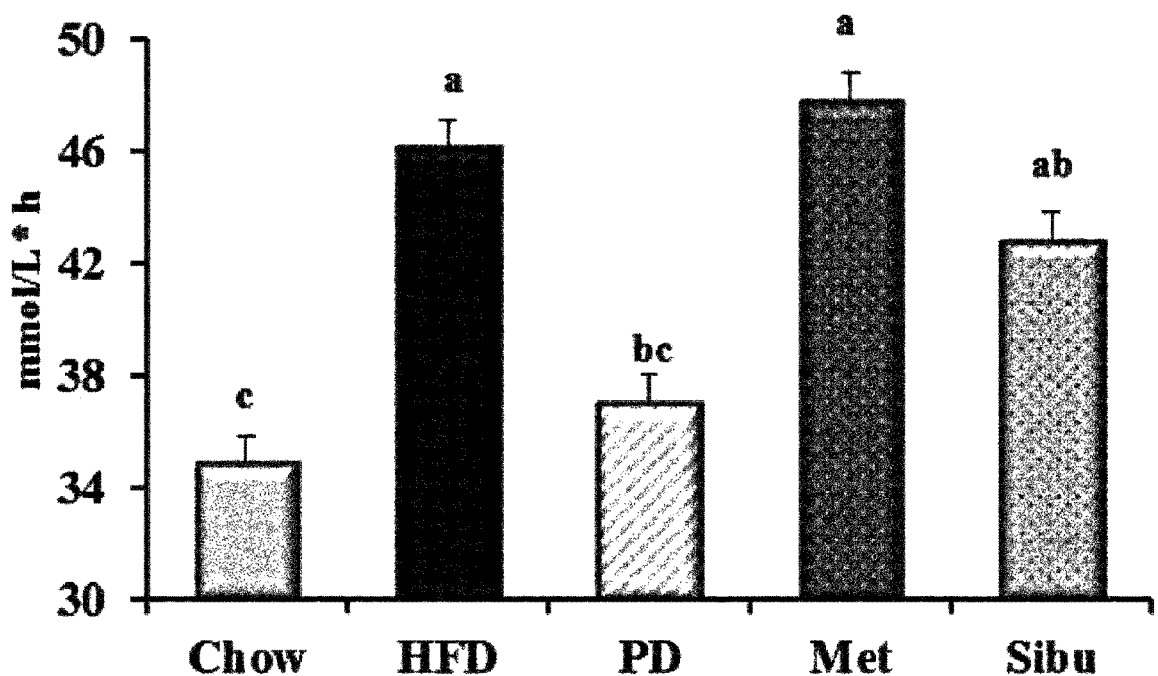
Figure 5C:
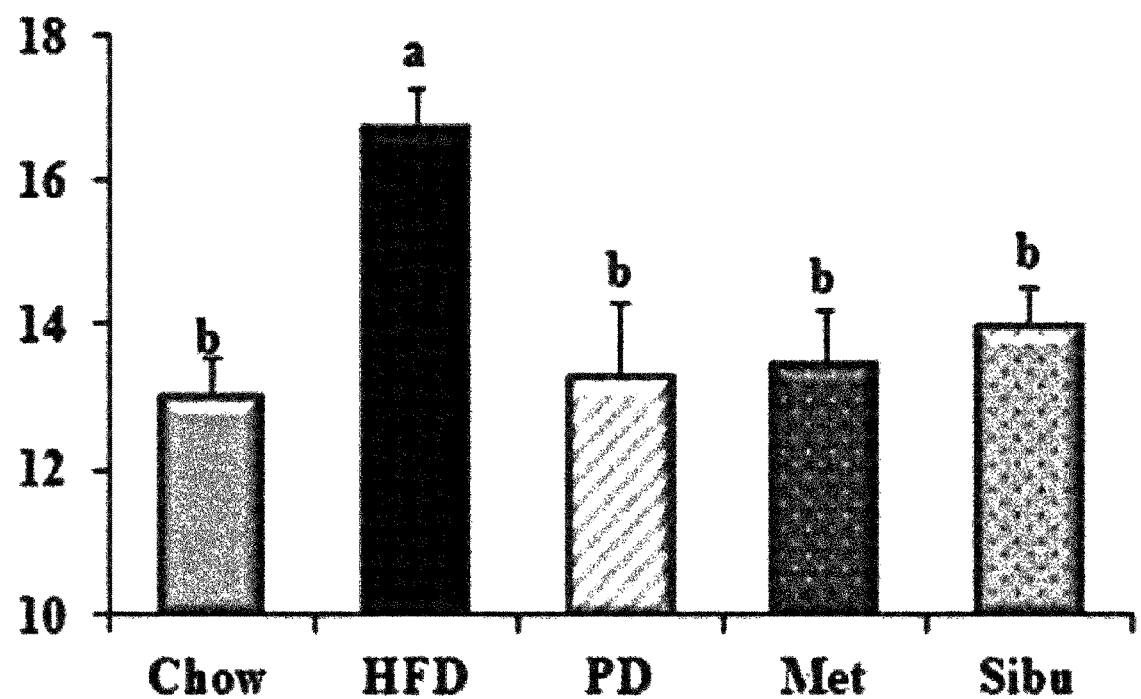
Figure 5D:
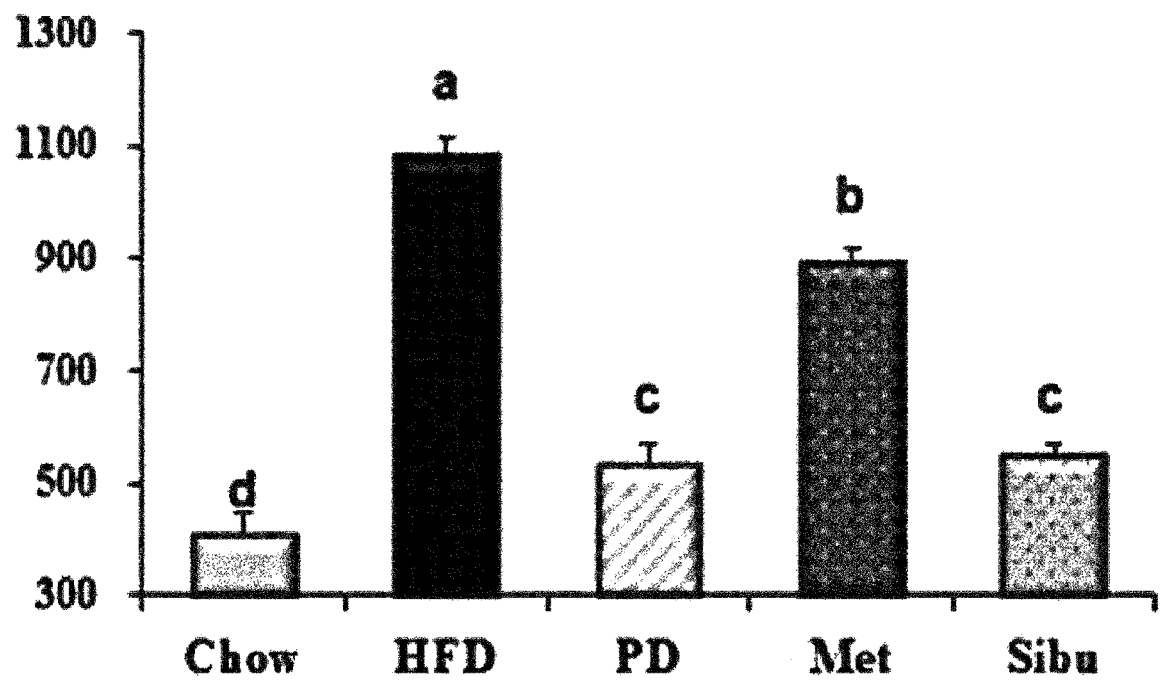
Figure 6A:
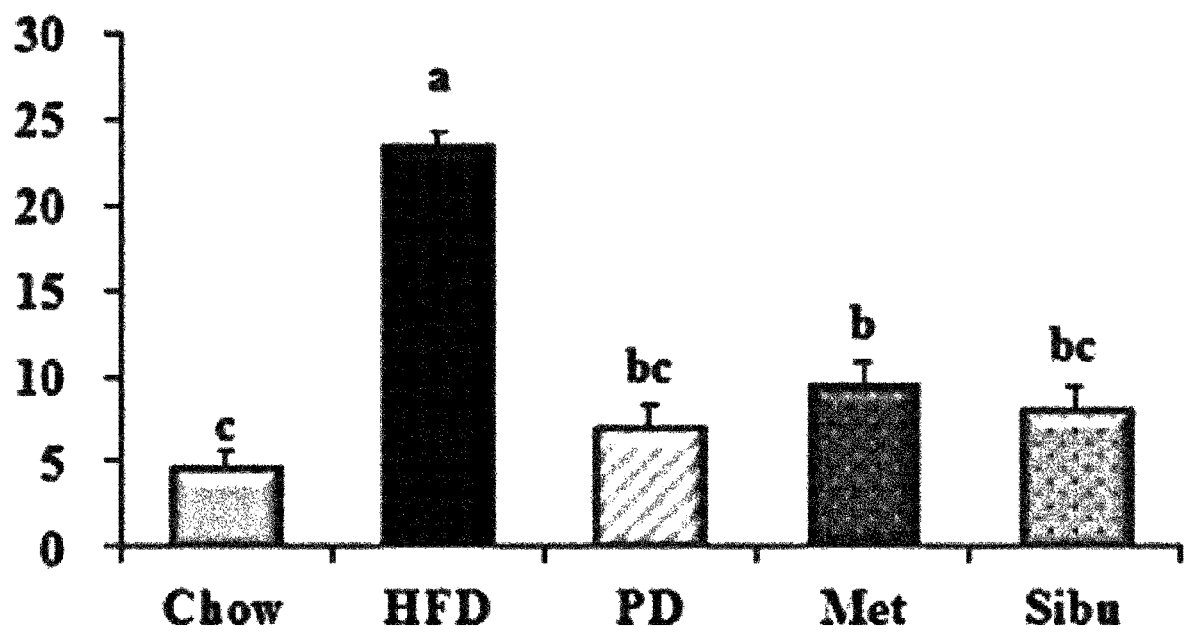
FIGS. 6A-6D shows inflammatory cytokine concentrations in blood of mice fed with the experimental diet (FIG. 6A: IL-6 (pg/mL), FIG. 6B: TNFα (pg/mL), FIG. 6C: MCP1 (pg/mL), and FIG. 6D: leptin (pg/mL)). Each value is a mean±standard deviation (SEM) of the measurement values of 8 mice. The letter on the same column indicates a significant difference within $P<0.05$ according to one-way ANOVA analysis and Duncan's multiple range test.
Figure 6B:
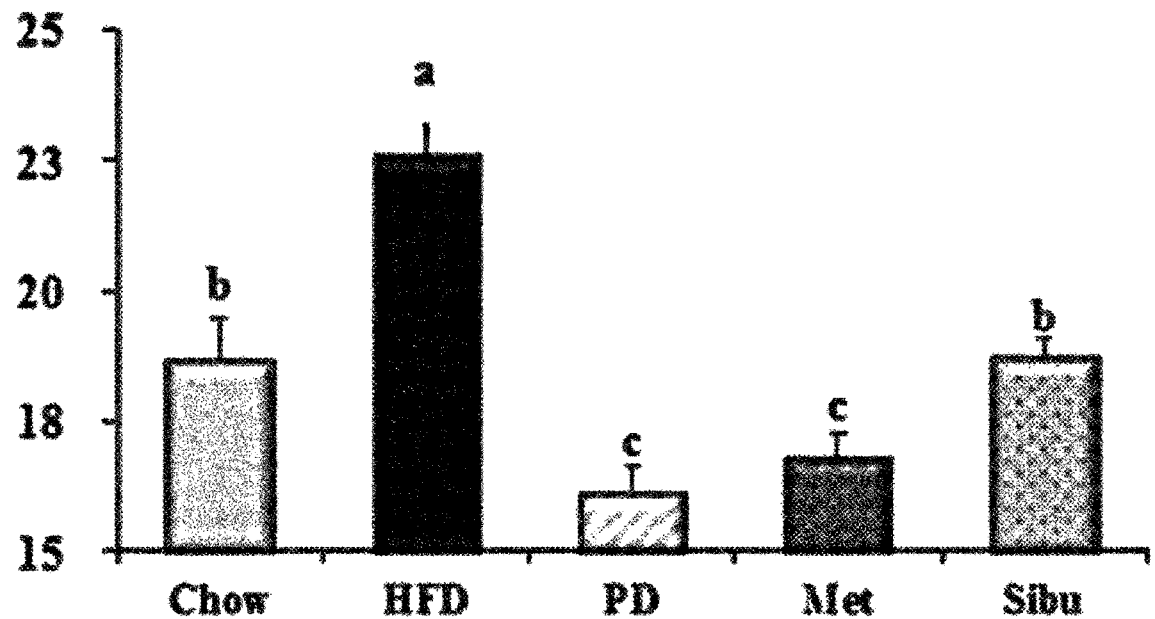
Figure 6C:
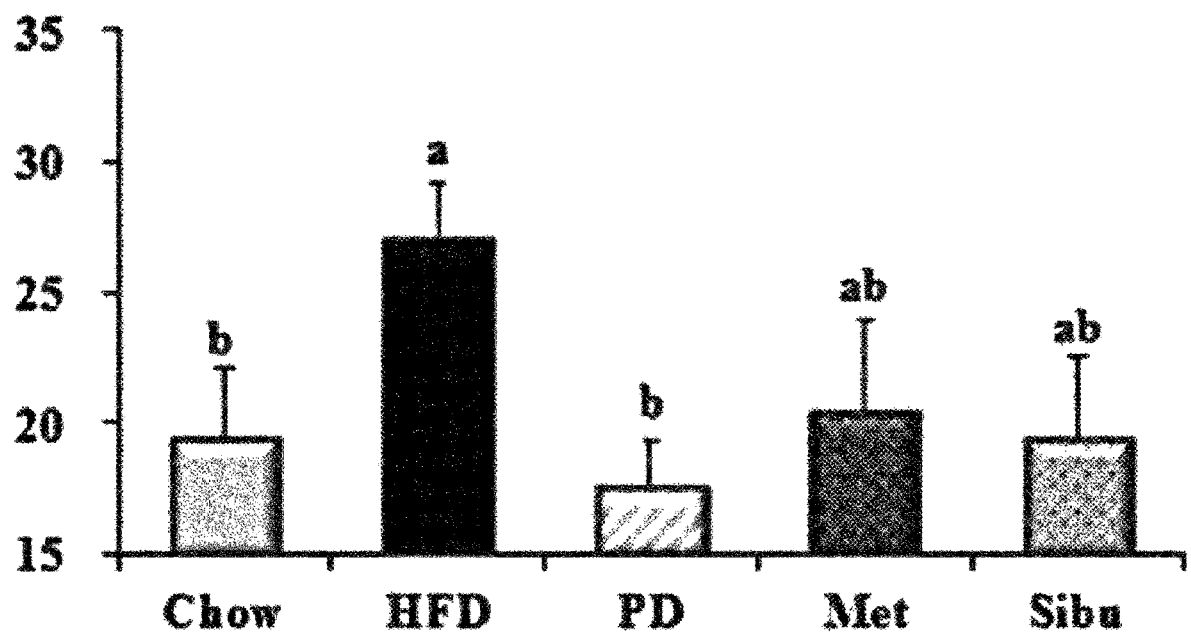
Figure 6D:
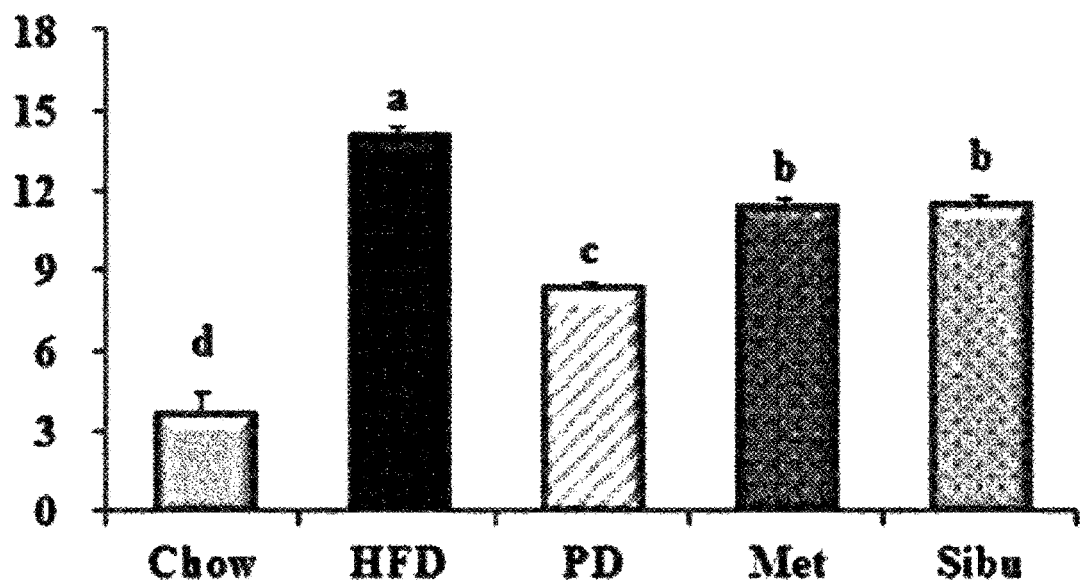

2) Changes in Index (Oral Glucose Resistance) Related to Type 2 Diabetes and Insulin Resistance Syndrome As a result of performing oral glucose tolerance tests for mice at 8 weeks of experimental raising (2 weeks before autopsy), compared to the HFD group, the PD group showed a decrease in blood glucose concentrations over time after sugar intake, and the area under the curve (AUC) of the glucose concentration was significantly reduced by 20% (FIGS. 5A and 5B). Meanwhile, the glucose and insulin concentrations of blood during fasting collected at the completion of experimental raising were significantly decreased by 21% and 50%, respectively, in the PD group, compared to the HFD group (FIGS. 5C and 5D).

Example 5: Effect of Pinocarveol on Alleviating Inflammation Activation in Dietary Obese Mice 1) Analysis Method of Concentration of Inflammatory Cytokine in Blood The concentrations of plasma IL-6, TNFα, MCP1, and leptin were measured by the ELISA method using the Milliplex map kit (Millipore Corporation, U.S.).

2) Changes in Concentration of Inflammatory Cytokine in Blood

Studies on the correlation between obesity and the immune system are actively carried out, for example, a new term of "metaflammation" was introduced for inflammatory responses caused by an oversupply of nutrients or metabolic substances, and obesity is interpreted as "chronic and low-level inflammation". As an example, in the case of toll-like receptor 4 (TLR4) involved in innate immune responses, dietary fat (particularly, saturated fatty acid) is used as a ligand to act as an important factor in inflammatory responses and insulin resistance pathway. When obesity is induced by high fat diet, it has been known that the amount of free fatty acids (particularly, saturated fatty acids) increases in body fluids, and when free fatty acids bind to TLR4 as ligands, IKK is activated to further activate NF-kB, which promotes the secretion of TNFα, IL-6, and the like which are proinflammatory cytokines to finally result in inflammatory responses. Besides, since TNFα and IL-6 activate cytokine signaling 3 (SOCS3) and JNK, it has been known that serine residues of insulin receptor substrate (IRS) are phosphorylated to suppress sugar transport, and as a result, insulin resistance is induced in peripheral tissues such as liver, muscle, or the like.

As a result of measuring the concentration of inflammatory cytokine in blood by the ELISA method, the PD group showed significant decreases in the concentrations of IL-6 (70%), TNFα (28%), MCP1 (35%), and leptin (40%), compared to the HFD group (FIGS. 6A-6D). Therefore, ingestion of pinocarveol significantly ameliorates inflammation activation induced by obesity.

Example 6: Expression Control of Genes and Proteins Related to Lipid Accumulation and Thermogenesis by Pinocarveol 1) RNA Separation and RT-PCR 1 mL of TRIzol solution was added per 0.1 g of adipose tissues of internal organs and hepatic tissues, and tissues were crushed and centrifuged at 4° C. and 12,000×g for 10 minutes. The supernatant was placed in a new tube, and 200 μL of chloroform was added followed by stirring. After repeating this procedure twice, the supernatant was placed in a new tube, and isopropanol and the supernatant were added at a ratio of 1:1. After strongly shaking for 10 times, the mixture was placed at room temperature for 10 minutes, centrifuged at 4° C. and 12,000×g for 10 minutes to remove the supernatant, and 1 mL of 70% ethanol was added to the precipitate to be centrifuged at 4° C. and 7,500×g for 5 minutes. After removing ethanol, the tube containing RNA precipitate was dried at room temperature for 5 minutes, and RNA pellet was dissolved using nuclease free water. By a using UV/VIS spectrophotometer (Beckman coulter, DU730, U.S.), the concentrations of RNA samples extracted at wavelengths of 260 nm and 280 nm were measured, and by carrying out agarose gel electrophoresis, the integrity of RNA samples was determined.

For RNA samples extracted from adipose tissues of internal organs and hepatic tissues, oligo dT primers and superscript reverse transcriptase (GIBCO BRL, U.S.) were used to carry out reverse transcription to synthesize cDNA. By using the cDNA obtained by reverse transcription as a ligand and using a 5' and 3' flanking sequence of the cDNA of the gene to be amplified as a primer, PCR was carried out, and at this time, the sequences of the used primers are shown in Table 2. 1 μL of the amplified PCR product was subject to electrophoresis on a 1% agarose gel to check for DNA bands.

TABLE 2

Primer sequences used for semi-quantitative RT-PCR analysis

| Gene | Primer | Sequence (5' → 3') | Annealing temperature (° C.) | PCR product (bp) |
|---|---|---|---|---|
| Peroxisome proliferator-activated receptor gamma 2 (PPARγ2) | F<br>R | TTCGGAATCAGCTCTGTGGA<br>CCATTGGGTCAGCTCTTGTG | 55 | 148 |
| CCAAT/enhancer binding protein alpha (C/EBPα) | F<br>R | TCGGTGCGTCTAAGATGAGG<br>TCAAGGCACATTTTTGCTCC | 55 | 187 |
| Cluster of differentiation 36 (CD36) | F<br>R | ATGACGTGGCAAAGAACAGC<br>GAAGGCTCAAAGATGGCTCC | 55 | 160 |
| Fatty acid synthase (FAS) | F<br>R | AGGGGTCGACCTGGTCCTCA<br>GCCATGCCCAGAGGGTGGTT | 65 | 132 |
| Lipoprotein lipase (leptin) | F<br>R | CTCCAAGGTTGTCCAGGGTT<br>AAAACTCCCCACAGAATGGG | 55 | 143 |
| Uncoupling protein 1 (UCP1) | F<br>R | GGTTTGCACCACACTOCTG<br>ACATGGACATCGCACAGCTT | 70 | 108 |
| Uncoupling protein 3 (UCP3) | F<br>R | ATGCTGAAGATGGTGGCTCA<br>TTGCCTTGTTCAAAACGGAG | 55 | 179 |
| Peroxisome proliferator-activated receptor-gamma coactivator 1 alpha (PFC1-α) | F<br>R | TAAATCTGCGGGATGATGGA<br>GTTTCGTTCGACCTGCGTAA | 67 | 109 |
| Sterol regulatory element-binding factor 1c (SREBP1C) | F<br>R | TTGTGGAGCTCAAAGACCTG<br>TGCAAGAAGCGGATGTAGTC | 55 | 94 |
| Liver X receptor (LXR) | F<br>R | TCCTACACGAGGATCAAGCG<br>AGTCGCAATGCAAAGACCTG | 55 | 119 |
| Lipoprotein lipase (LPL) | F<br>R | TGCCGCTGTTTTGTTTTACC<br>TCACAGTTTCTGCTCCCAGC | 55 | 172 |
| Acetyl-CoA carboxylase (ACC) | F<br>R | TGATGTCAATCTCCCCGCAGC<br>TTGCTTCTTCTCTGTTTTCTCC<br>C | 60 | 353 |
| Glyceraldehyde-3-phosphate dehydrogenase (GAPDH) | F<br>R | AGAACATCATCCCTGCATCC<br>TCCACCACCCTGTTGCTGTA | 55 | 321 |

2) Western Blot Analysis

A predetermined amount of visceral fat or hepatic tissues was homogenized with liquid nitrogen and a lysis buffer solution in a mortar and centrifuged at 13,000×g and 4° C. for 20 minutes, and the middle layer was obtained to quantify proteins according to the Bradford method. 50 μg of the protein was subject to electrophoresis on an SDS polyacrylamide gel, was subject to electroblotting on a PVDF hyper film, and was reacted with the corresponding antibody, β-catenin, phospho-AMPK (AMP-activated protein kinase), AMPK, GAPDH (Cell-Signaling Technology, U.S.), respectively. The signal of each protein was visualized by a chemiluminescent detection system (Amersham, U.K.), and the thickness of bands was quantified by using the Quantity One Analysis Software (Bio-Rad Laboratories, U.S.).

Figure 7A:
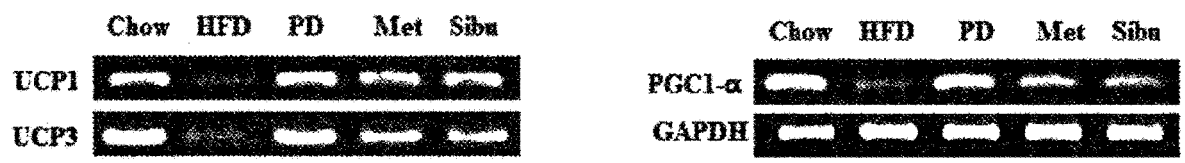
FIGS. 7A-7C shows changes in the expressions of genes and proteins related to thermogenesis (FIG. 7A) and adipogenesis (FIG. 7B) in adipose tissues of internal organs of mice. The upper panel is a representative gel image of RT-PCR analysis, and the lower panel indicates relative expression amounts of the genes. Data were standardized based on GAPDH mRNA levels, and all expression levels were expressed as values relative to normal diet mice. The upper panel of FIG. 7C is a representative gel image of western blot analysis, and the lower panel indicates relative expression amounts of the proteins. Data were standardized based on GAPDH levels, and all expression levels were expressed as values relative to normal diet mice. The results are indicated as results for three independent experiments using an RNA sample pool of 8 mice. The letter on the graph bar indicates a significant difference from other diet groups within $P<0.05$ according to one-way ANOVA analysis and Duncan's multiple range test.
Figure 7A:
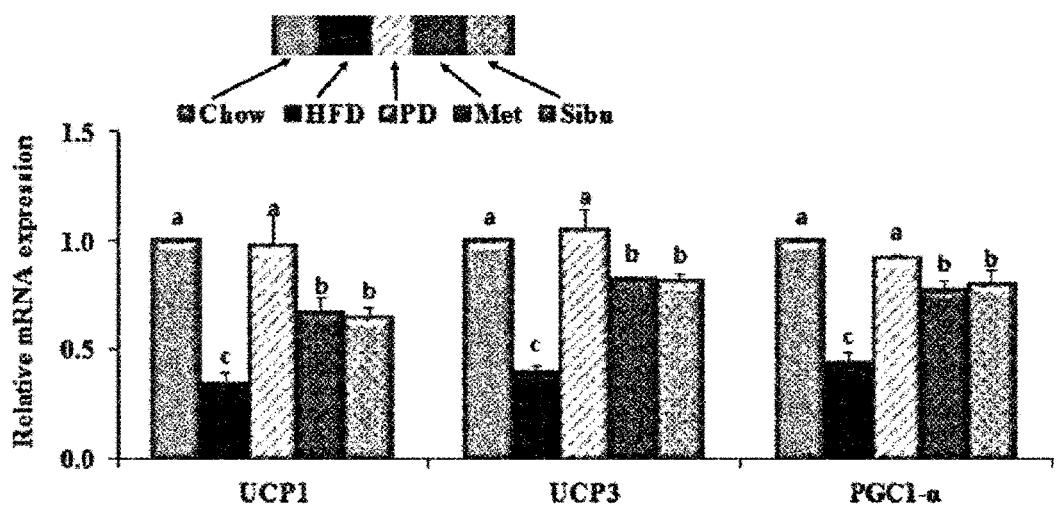

3) Changes in Expression of Gene and Proteins of Adipose Tissues of Internal Organs As a result of measuring expressions of genes (UCP1 and UCP3) and a transcriptional regulatory factor (PGC-1α) related to thermogenesis in adipose tissues of internal organs using RT-PCR, the HFD group showed a significant decrease in the expression of the genes related to thermogenesis compared to the normal diet group. The supplemental intake of pinocarveol significantly increased all of the gene expressions of UCP1, UCP3, and PGC-1α, which had been decreased by an intake of high fat diet (FIG. 7A).

Figure 7B:
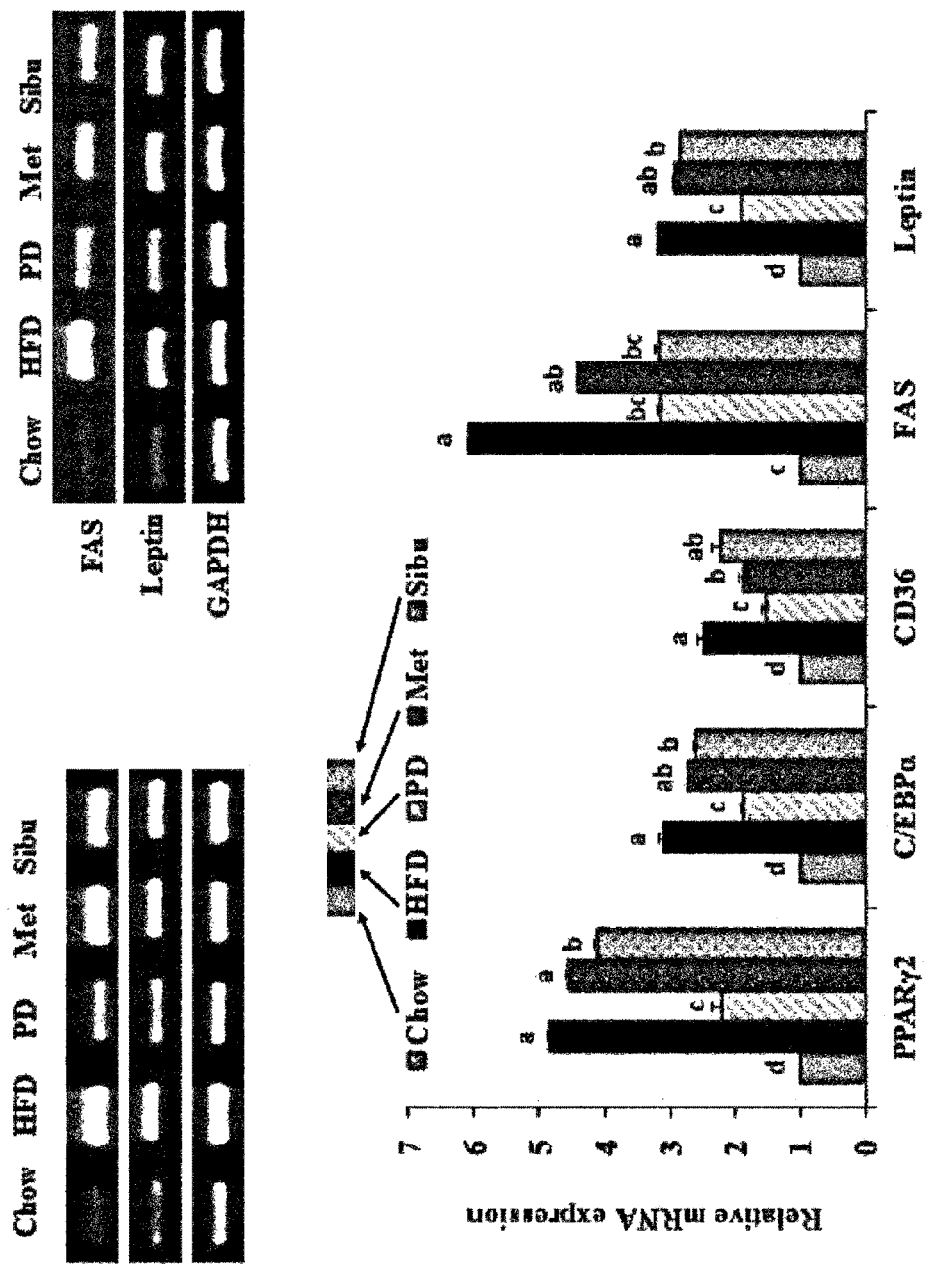
Figure 7C:
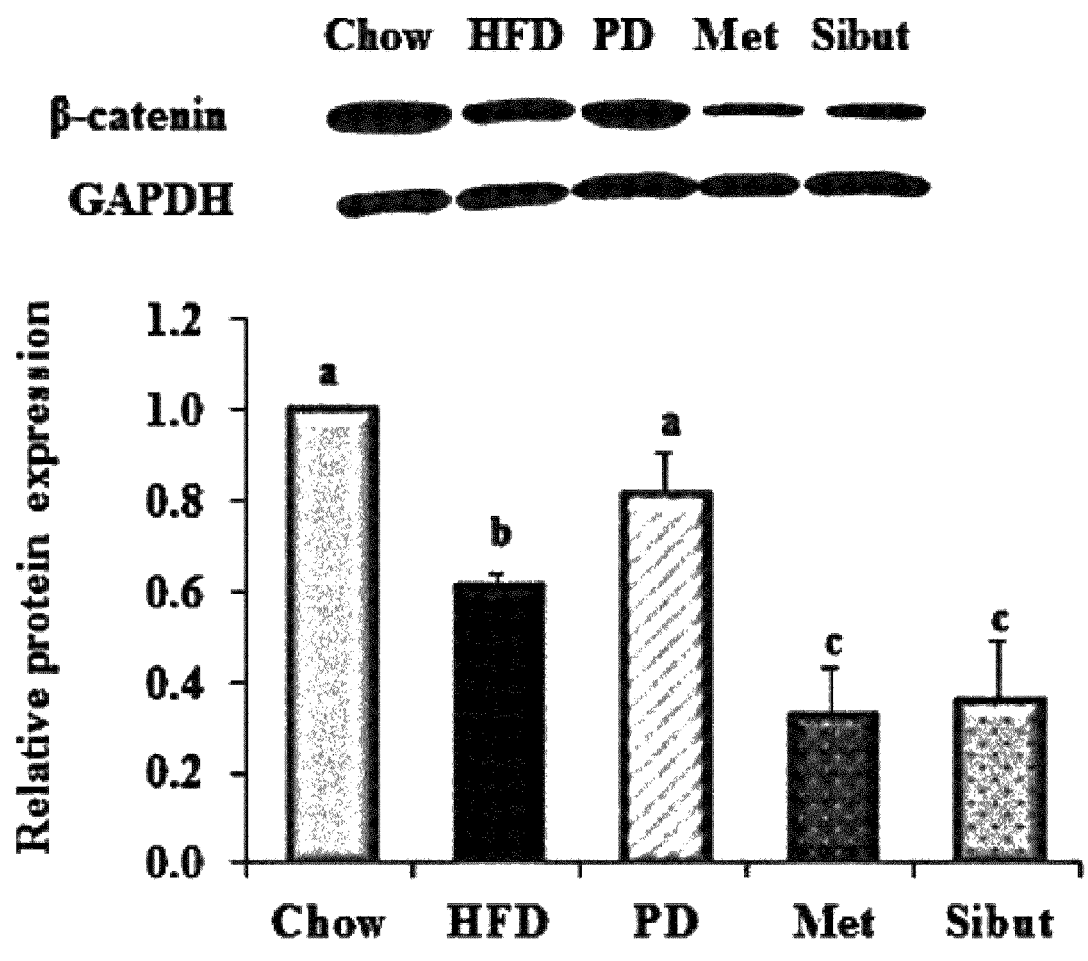

In addition, the HFD group showed a significant increase in all of the expressions of C/EBPα and PPARγ2 which are nuclear transcription factors which have an important role in adipogenesis, and CD36, FAS, and leptin which are target genes of the transcription factors, compared to the normal diet group. As a result of supplemental feeding of pinocarveol to mice fed with the high fat diet, all of the expressions of nuclear transcription factors and target genes thereof, which had been increased due to an intake of the high fat diet, significantly decreased in adipose tissues of internal organs (FIG. 7B). As a result of evaluating the protein expression amount of β-catenin which is an upstream signal transduction substance controlling lipogenesis in adipose tissues of internal organs by using western blot, the PD group showed a significant increase compared to the HFD group (FIG. 7C). Therefore, it was found that the supplemental feeding of pinocarveol reduced expressions of the nuclear transcription factors and the target genes thereof which serve a pivotal role in lipogenesis in adipose tissues of internal organs and increased the protein expression of β-catenin, thereby preventing the accumulation of visceral fat.

4) Changes in Expressions of Genes and Proteins in Hepatic Tissues

Figure 8A:
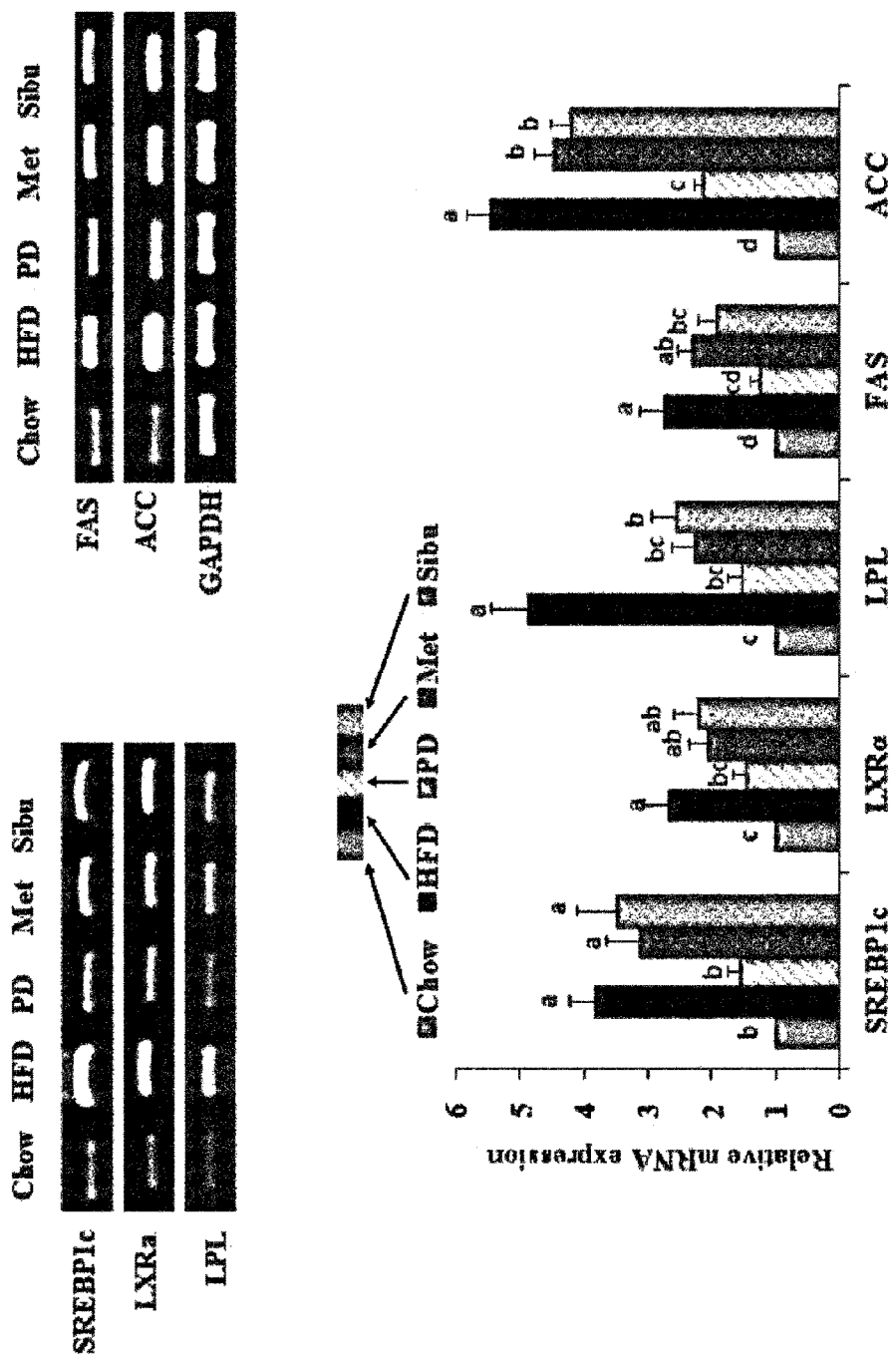
FIGS. 8A-8B are images showing changes in the expressions of genes and proteins related to lipogenesis in hepatic tissues of mice. The upper panel of FIG. 8A is a representative gel image of RT-PCR analysis, and the lower panel indicates relative expression amounts of the genes. Data were standardized based on GAPDH mRNA levels, and all expression levels were expressed as values relative to normal diet mice. The upper panel of FIG. 8B is a representative gel image of western blot analysis of p-AMPK and AMPK, and the lower panel indicates relative ratios of the expressions of p-AMPK/AMPK proteins in hepatic tissues. Data were standardized based on GAPDH levels, and all expression levels were expressed as values relative to normal diet mice. The results are indicated as results for three independent experiments using an RNA sample pool of 8 mice. The letter on the graph bar indicates a significant difference from other diet groups within $P<0.05$ according to one-way ANOVA analysis and Duncan's multiple range test.
Figure 8B:
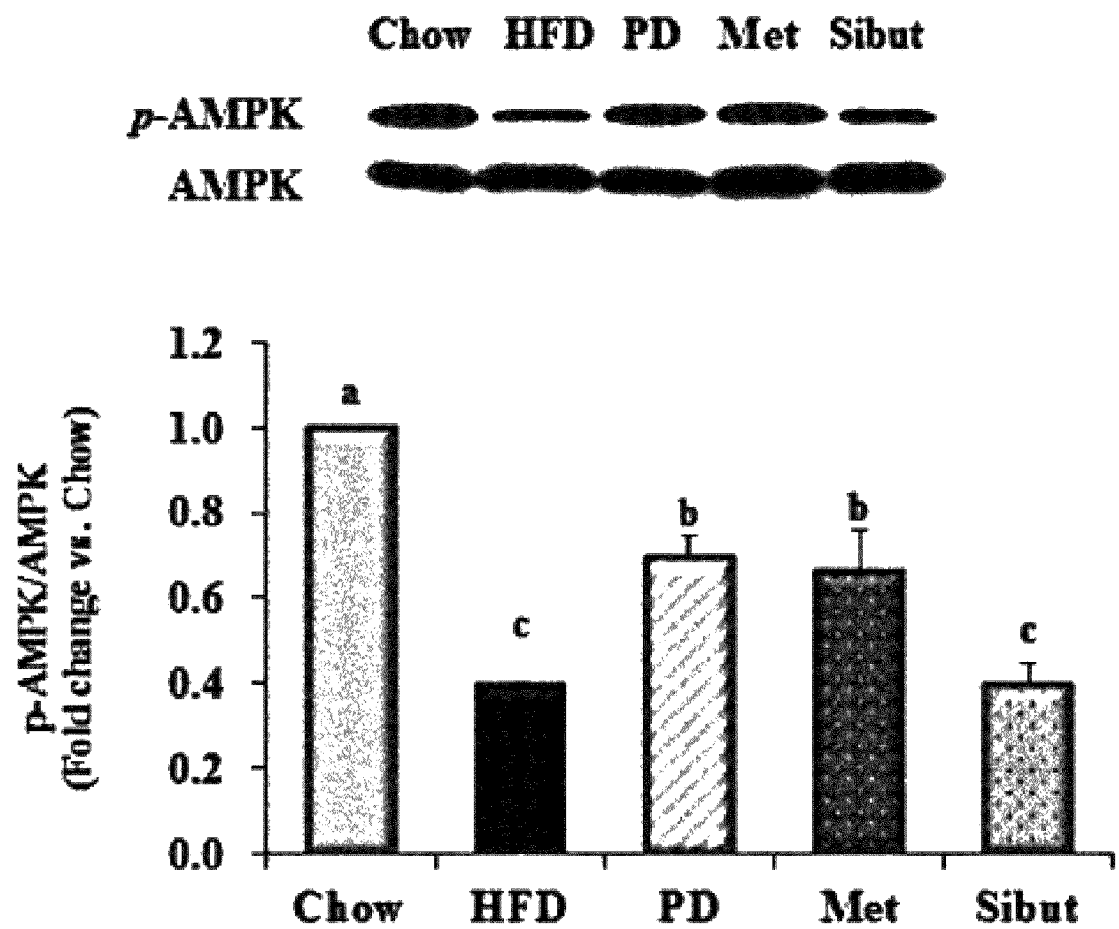

As a result of evaluating the degree of mRNA expressions of hepatic tissues using RT-PCR, the HFD group showed significant increases in all of the expressions of SREBP and LXRα which are nuclear transcription factors that have an important role in lipogenesis, and LPL, FAS, and ACC which are target genes of the transcription factors, compared to the normal control group. Meanwhile, as a result of supplemental feeding of pinocarveol, all of the expressions of the nuclear transcription factors and target genes thereof, which had been increased due to an intake of the high fat diet, significantly decreased in hepatic tissues (FIG. 8A). As a result of evaluating the activation (p-AMPK/AMPK ratio) of AMPK which is a signal transduction substance promoting the oxidation of fatty acids in hepatic tissues by using western blot, the PD group showed a significant increase compared to the HFD group (FIG. 8B). Therefore, it was found that the supplemental feeding of pinocarveol reduced expressions of the nuclear transcription factors and the target genes thereof which serve a pivotal role in lipogenesis in hepatic tissues and increased the activation of signal transduction substances which promote oxidation of fatty acids, thereby exhibiting an effect of ameliorating fatty liver induced by obesity.

While specific parts of the present invention have been described in detail, these specific techniques are only preferred embodiments for those having ordinary skill in the art, and it is apparent that the scope of the invention is not limited thereto. Therefore, the substantial scope of the present invention may be defined by the appended claims and their equivalents.

The invention claimed is:

1. A method of treating a metabolic disease, the method comprising:
   administering a pharmaceutical composition comprising isolated or purified pinocarveol as an active ingredient to a subject in need thereof,
   wherein the metabolic disease is obesity, diabetes, dyslipidemia, fatty liver, or insulin resistance syndrome,
   wherein the subject in need thereof has the metabolic disease and the metabolic disease is treated,
   wherein the subject in need thereof has a reduction in body weight, and wherein the isolated or purified pinocarveol does not suppress the subject's appetite, and
   wherein 0.0001 to 1,000 mg/kg per day of the pharmaceutical composition is administered to the subject.

2. The method of claim 1, wherein the dyslipidemia is hyperlipidemia.

3. The method of claim 1, wherein the fatty liver is non-alcoholic fatty liver.

4. The method of claim 1, wherein the pharmaceutical composition reduces body weight, diet efficiency, visceral fat, a plasma lipid concentration, liver weight or a lipid concentration in a liver tissue.

5. The method of claim 1, wherein the pharmaceutical composition reduces alanine aminotransferase (ALT) activity or aspartate aminotransferase (AST) activity in blood.

6. The method of claim 1, wherein the pharmaceutical composition reduces a fasting blood sugar concentration, a fasting insulin concentration in blood or an inflammatory cytokine concentration in blood.

7. The method of claim 1, wherein the pharmaceutical composition increases expression of uncoupling protein 1 (UCP1), uncoupling protein 3 (UCP3), peroxisome proliferator-activated receptor-gamma coactivator 1 alpha (PGC- 1α), or (β-catenin, or activity of AMP-activated protein kinase (AMPK); or reduces expression of CCAAT enhancer-binding proteins (C/EBPα), peroxisome proliferator-activated receptor gamma (PPARγ), cluster of differentiation 36 (CD36), fatty acid synthase (FAS), leptin, sterol regulatory element-binding factor 1c (SREBP1C), liver X receptor alpha (LXRα), lipoprotein lipase (LPL), or acetyl-CoA carboxylase (ACC), in visceral fat or the liver.

8. The method of claim 1, wherein the metabolic disease is obesity.

* * * * *

SEQUENCE LISTING

<160> NUMBER OF SEQ ID NOS: 26

<210> SEQ ID NO 1
<211> LENGTH: 20
<212> TYPE: DNA
<213> ORGANISM: Artificial Sequence
<220> FEATURE:
<223> OTHER INFORMATION: Peroxisome proliferator-activated receptor
      gamma 2_F primer

<400> SEQUENCE: 1
ttcggaatca gctctgtgga                                          20

<210> SEQ ID NO 2
<211> LENGTH: 20
<212> TYPE: DNA
<213> ORGANISM: Artificial Sequence
<220> FEATURE:
<223> OTHER INFORMATION: Peroxisome proliferator-activated receptor
      gamma 2_R primer

<400> SEQUENCE: 2
ccattgggtc agctcttgtg                                          20

```
<210> SEQ ID NO 3
<211> LENGTH: 20
<212> TYPE: DNA
<213> ORGANISM: Artificial Sequence
<220> FEATURE:
<223> OTHER INFORMATION: CCAAT/enhancer binding protein alpha_F primer

<400> SEQUENCE: 3
tcggtgcgtc taagatgagg                                                   20

<210> SEQ ID NO 4
<211> LENGTH: 20
<212> TYPE: DNA
<213> ORGANISM: Artificial Sequence
<220> FEATURE:
<223> OTHER INFORMATION: CCAAT/enhancer binding protein alpha_R primer

<400> SEQUENCE: 4
tcaaggcaca ttttttgctcc                                                  20

<210> SEQ ID NO 5
<211> LENGTH: 20
<212> TYPE: DNA
<213> ORGANISM: Artificial Sequence
<220> FEATURE:
<223> OTHER INFORMATION: Cluster of differentiation 36_F primer

<400> SEQUENCE: 5
atgacgtggc aaagaacagc                                                   20

<210> SEQ ID NO 6
<211> LENGTH: 20
<212> TYPE: DNA
<213> ORGANISM: Artificial Sequence
<220> FEATURE:
<223> OTHER INFORMATION: Cluster of differentiation 36_R primer

<400> SEQUENCE: 6
gaaggctcaa agatggctcc                                                   20

<210> SEQ ID NO 7
<211> LENGTH: 20
<212> TYPE: DNA
<213> ORGANISM: Artificial Sequence
<220> FEATURE:
<223> OTHER INFORMATION: Fatty acid synthase_F primer

<400> SEQUENCE: 7
aggggtcgac ctggtcctca                                                   20

<210> SEQ ID NO 8
<211> LENGTH: 20
<212> TYPE: DNA
<213> ORGANISM: Artificial Sequence
<220> FEATURE:
<223> OTHER INFORMATION: Fatty acid synthase_R primer

<400> SEQUENCE: 8
gccatgccca gagggtggtt                                                   20

<210> SEQ ID NO 9
<211> LENGTH: 20
<212> TYPE: DNA
<213> ORGANISM: Artificial Sequence
<220> FEATURE:
<223> OTHER INFORMATION: Lipoprotein lipase_F primer
```

```
<400> SEQUENCE: 9
ctccaaggtt gtccagggtt                                              20

<210> SEQ ID NO 10
<211> LENGTH: 20
<212> TYPE: DNA
<213> ORGANISM: Artificial Sequence
<220> FEATURE:
<223> OTHER INFORMATION: Lipoprotein lipase_R primer

<400> SEQUENCE: 10
aaaactcccc acagaatggg                                              20

<210> SEQ ID NO 11
<211> LENGTH: 18
<212> TYPE: DNA
<213> ORGANISM: Artificial Sequence
<220> FEATURE:
<223> OTHER INFORMATION: Uncoupling protein 1_F primer

<400> SEQUENCE: 11
ggtttgcacc acactctg                                                18

<210> SEQ ID NO 12
<211> LENGTH: 20
<212> TYPE: DNA
<213> ORGANISM: Artificial Sequence
<220> FEATURE:
<223> OTHER INFORMATION: Uncoupling protein 1_R primer

<400> SEQUENCE: 12
acatggacat cgcacagctt                                              20

<210> SEQ ID NO 13
<211> LENGTH: 20
<212> TYPE: DNA
<213> ORGANISM: Artificial Sequence
<220> FEATURE:
<223> OTHER INFORMATION: Uncoupling protein 3_F primer

<400> SEQUENCE: 13
atgctgaaga tggtggctca                                              20

<210> SEQ ID NO 14
<211> LENGTH: 20
<212> TYPE: DNA
<213> ORGANISM: Artificial Sequence
<220> FEATURE:
<223> OTHER INFORMATION: Uncoupling protein 3_R primer

<400> SEQUENCE: 14
ttgccttgtt caaaacggag                                              20

<210> SEQ ID NO 15
<211> LENGTH: 20
<212> TYPE: DNA
<213> ORGANISM: Artificial Sequence
<220> FEATURE:
<223> OTHER INFORMATION: Peroxisome proliferator-activated receptor-
      gamma coactivator 1 alpha_F primer

<400> SEQUENCE: 15
taaatctgcg ggatgatgga                                              20
```

```
<210> SEQ ID NO 16
<211> LENGTH: 20
<212> TYPE: DNA
<213> ORGANISM: Artificial Sequence
<220> FEATURE:
<223> OTHER INFORMATION: Peroxisome proliferator-activated receptor-
      gamma coactivator 1 alpha_R primer

<400> SEQUENCE: 16
gtttcgttcg acctgcgtaa                                                   20

<210> SEQ ID NO 17
<211> LENGTH: 20
<212> TYPE: DNA
<213> ORGANISM: Artificial Sequence
<220> FEATURE:
<223> OTHER INFORMATION: Sterol regulatory element-binding factor 1c_F
      primer

<400> SEQUENCE: 17
ttgtggagct caaagacctg                                                   20

<210> SEQ ID NO 18
<211> LENGTH: 20
<212> TYPE: DNA
<213> ORGANISM: Artificial Sequence
<220> FEATURE:
<223> OTHER INFORMATION: Sterol regulatory element-binding factor 1c_R
      primer

<400> SEQUENCE: 18
tgcaagaagc ggatgtagtc                                                   20

<210> SEQ ID NO 19
<211> LENGTH: 20
<212> TYPE: DNA
<213> ORGANISM: Artificial Sequence
<220> FEATURE:
<223> OTHER INFORMATION: Liver X receptor_F primer

<400> SEQUENCE: 19
tcctacacga ggatcaagcg                                                   20

<210> SEQ ID NO 20
<211> LENGTH: 20
<212> TYPE: DNA
<213> ORGANISM: Artificial Sequence
<220> FEATURE:
<223> OTHER INFORMATION: Liver X receptor_R primer

<400> SEQUENCE: 20
agtcgcaatg caaagacctg                                                   20

<210> SEQ ID NO 21
<211> LENGTH: 20
<212> TYPE: DNA
<213> ORGANISM: Artificial Sequence
<220> FEATURE:
<223> OTHER INFORMATION: Lipoprotein lipase_F primer

<400> SEQUENCE: 21
tgccgctgtt ttgttttacc                                                   20

<210> SEQ ID NO 22
<211> LENGTH: 20
<212> TYPE: DNA
<213> ORGANISM: Artificial Sequence
```

```
<220> FEATURE:
<223> OTHER INFORMATION: Lipoprotein lipase_R primer

<400> SEQUENCE: 22
tcacagtttc tgctcccagc                                              20

<210> SEQ ID NO 23
<211> LENGTH: 21
<212> TYPE: DNA
<213> ORGANISM: Artificial Sequence
<220> FEATURE:
<223> OTHER INFORMATION: Acetyl-CoA carboxylase_F primer

<400> SEQUENCE: 23
tgatgtcaat ctccccgcag c                                            21

<210> SEQ ID NO 24
<211> LENGTH: 23
<212> TYPE: DNA
<213> ORGANISM: Artificial Sequence
<220> FEATURE:
<223> OTHER INFORMATION: Acetyl-CoA carboxylase_R primer

<400> SEQUENCE: 24
ttgcttcttc tctgttttct ccc                                          23

<210> SEQ ID NO 25
<211> LENGTH: 20
<212> TYPE: DNA
<213> ORGANISM: Artificial Sequence
<220> FEATURE:
<223> OTHER INFORMATION: Glyceraldehyde-3-phosphate dehydrogenase_F
      primer

<400> SEQUENCE: 25
agaacatcat ccctgcatcc                                              20

<210> SEQ ID NO 26
<211> LENGTH: 20
<212> TYPE: DNA
<213> ORGANISM: Artificial Sequence
<220> FEATURE:
<223> OTHER INFORMATION: Glyceraldehyde-3-phosphate dehydrogenase_R
      primer

<400> SEQUENCE: 26
tccaccaccc tgttgctgta                                              20
```